(12) United States Patent
Nomura et al.

(10) Patent No.: US 11,471,065 B2
(45) Date of Patent: Oct. 18, 2022

(54) MEDICAL IMAGE DIAGNOSIS APPARATUS

(71) Applicant: CANON MEDICAL SYSTEMS CORPORATION, Otawara (JP)

(72) Inventors: Ei Nomura, Tsukuba (JP); Hitoshi Kanazawa, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 943 days.

(21) Appl. No.: 15/974,957

(22) Filed: May 9, 2018

(65) Prior Publication Data

US 2018/0325411 A1 Nov. 15, 2018

(30) Foreign Application Priority Data

May 12, 2017 (JP) .............................. JP2017-095651

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/316* (2021.01); *A61B 5/349* (2021.01); *A61B 5/7292* (2013.01);
(Continued)

(58) Field of Classification Search
None
See application file for complete search history.

(56) References Cited

U.S. PATENT DOCUMENTS 4,676,253 A * 6/1987 Newman ................ A61B 5/029
600/506
9,500,732 B2 11/2016 Yoshizawa et al.
(Continued)

FOREIGN PATENT DOCUMENTS

JP 61-119251 A 6/1986
JP 2010-220859 A 10/2010
(Continued)

OTHER PUBLICATIONS

Jacquemet et al. ("Evaluation of a subject-specific transfer function based nonlinear QT interval rate-correction method", Physiol. Meas. 32, 619-635 (Year: 2011).*
(Continued)

*Primary Examiner* — Amelie R Davis
*Assistant Examiner* — Marjan Saboktakin
(74) *Attorney, Agent, or Firm* — Oblon, McClelland, Maier & Neustadt, L.L.P.

(57) ABSTRACT

A medical image diagnosis apparatus according to an embodiment includes processing circuitry. The processing circuitry is configured to derive a subject-specific regression model that indicates a relationship among a cardiac cycle, systole, and diastole of the subject. The processing circuitry is configured to derive timing of a data acquisition in a synchronization imaging performed in synchronization with heartbeats of the heart of the subject, by using the derived regression model and electrocardiographic information of the subject obtained during an image taking process. The processing circuitry is configured to control the synchronization imaging so that the data acquisition is performed with the derived timing.

19 Claims, 10 Drawing Sheets

(51) Int. Cl.

| | | |
|---|---|---|
| *A61B 5/316* | (2021.01) | |
| *A61B 5/349* | (2021.01) | |
| *G01R 33/567* | (2006.01) | |
| *G01R 33/48* | (2006.01) | |
| *G01R 33/563* | (2006.01) | |
| *G01R 33/54* | (2006.01) | |

(52) U.S. Cl.
CPC ..... *G01R 33/4822* (2013.01); *G01R 33/5673* (2013.01); *G01R 33/543* (2013.01); *G01R 33/5635* (2013.01); *G01R 33/5676* (2013.01)

(56) References Cited

U.S. PATENT DOCUMENTS

| | | | |
|---|---|---|---|
| 2009/0234239 A1* | 9/2009 | Shani | A61B 5/25 |
| | | | 600/516 |
| 2017/0332981 A1* | 11/2017 | Witschey | G01R 33/5673 |

FOREIGN PATENT DOCUMENTS

| | | | |
|---|---|---|---|
| JP | 2011-036325 | * | 2/2011 |
| JP | 5371620 | | 12/2013 |
| WO | WO2012/102338 | | 8/2012 |

OTHER PUBLICATIONS

Roes et al. ("Correction for heart rate variability during 3D whole heart MR coronary aniography", J. of Mag. Imag. 27: 1046-1053 (2008)) (Year: 2008).*

Plein, S., et al. "Three-Dimensional Coronary MR Angiography Performed with Subject-Specific Cardiac Acquisition Windows and Motion-Adapted Respiratory Gating", American Journal of Roentgenology, 180(2):505-12, 2003.

Roes, S., et al. "Correction for Heart Rate Variability During 3D Whole Heart MR Coronary Angiography", Journal of Magnetic Resonance Imaging, 27(5): 1046-53, 2008.

Malik, M., et al. "Relation between QT and RR intervals is highly individual among healthy subjects: implications for heart rate correction of the QT interval", Heart, 87(3):220-228, 2002.

Batchvarov, V., et al. "QT-RR relationship in healthy subjects exhibits substantial intersubject variability and high intrasubject stability", American Journal of Physiology—Heart and Circulatory Physiology, 282: H2356-H2363, 2002.

Ishida, S., et al. "Relation between QT and RR intervals in patients with bradyarrhythmias", British Heart Journal, 74:159-162, 1995.

Jacquemet, V., et al. "Evaluation of a subject-specific transfer-function-based nonlinear QT interval rate-correction method", Physiological Measurement, 32, 619-635, 2011.

Cabasson, A., et al. "Estimation and Modeling of QT-interval Adaption to Heart Rate Changes", IEEE Transactions on Biomedical Engineering, vol. 59, Issue 4, 2012, 8 pages.

Japanese Office Action dated Mar. 15, 2022 in Japanese Patent Application No. 2018-090519, 5 pages.

* cited by examiner

MEDICAL IMAGE DIAGNOSIS APPARATUS

CROSS-REFERENCE TO RELATED APPLICATIONS

This application is based upon and claims the benefit of priority from Japanese Patent Application No. 2017-095651, filed on May 12, 2017, the entire contents of which are incorporated herein by reference.

FIELD

Embodiments described herein relate generally to a medical image diagnosis apparatus.

BACKGROUND

Conventionally, in medical examinations performed on the heart or the like by using a medical image diagnosis apparatus such as a magnetic resonance imaging apparatus, a synchronization imaging may be performed in some situations to acquire data from a subject in synchronization with heartbeats. Further, techniques are known with which, during such a synchronization imaging, it is possible to reduce degradation in image quality caused by fluctuation of heartbeats of the subject.

DETAILED DESCRIPTION

A medical image diagnosis apparatus according to an embodiment includes a first deriving unit, a second deriving unit, and a controlling unit. The first deriving unit is configured to derive a subject-specific regression model that indicates a relationship among a cardiac cycle, systole, and diastole of the subject. The second deriving unit is configured to derive timing of a data acquisition in a synchronization imaging performed in synchronization with heartbeats of the heart of the subject, by using the derived regression model and electrocardiographic information of the subject obtained during an image taking process. The controlling unit is configured to control the synchronization imaging so that the data acquisition is performed with the derived timing.

In the embodiments described below, examples will be explained in which the abovementioned configuration of the medical image diagnosis apparatus is applied to a Magnetic Resonance Imaging (MRI) apparatus.

First Embodiment

Figure 1:
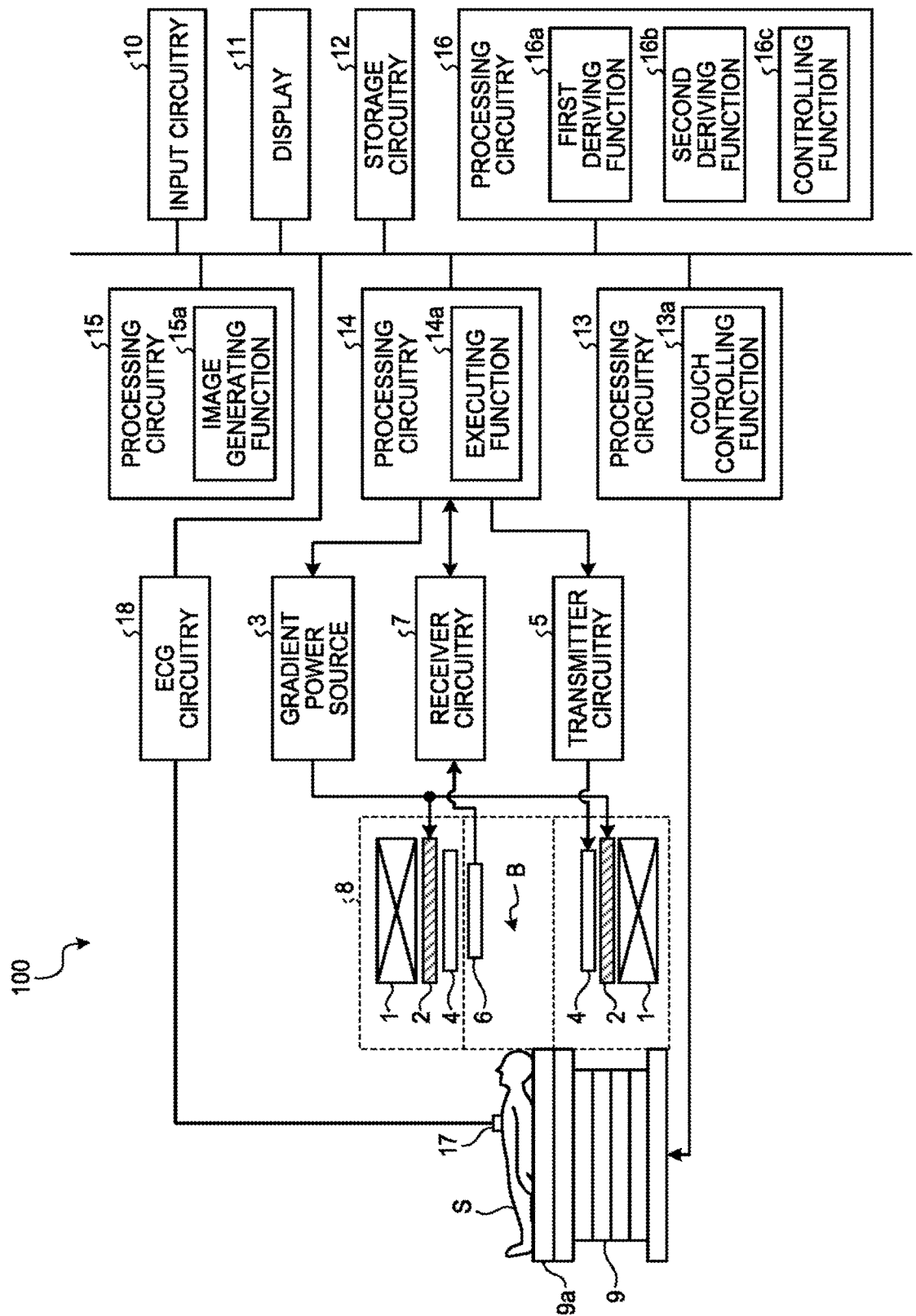
FIG. 1 is a diagram illustrating an exemplary configuration of a Magnetic Resonance Imaging (MRI) apparatus according to a first embodiment.

FIG. 1 is a diagram illustrating an exemplary configuration of an MRI apparatus according to a first embodiment. For example, as illustrated in FIG. 1, an MRI apparatus 100 according to the first embodiment includes a static magnetic field magnet 1, a gradient coil 2, a gradient power source 3, a transmission coil 4, transmitter circuitry 5, a receiver coil 6, receiver circuitry 7, a gantry 8, a couch 9, input circuitry 10, a display 11, storage circuitry 12, pieces of processing circuitry 13 to 16, an electrocardiogram (ECG) sensor 17, and ECG circuitry 18.

The static magnetic field magnet 1 is formed to have a hollow and substantially circular cylindrical shape (which may have an oval cross-section orthogonal to the central axis thereof) and is configured to generate a uniform static magnetic field in the space on the inside thereof. For example, the static magnetic field magnet 1 includes a vacuum container formed to have a substantially circular cylindrical shape and a magnet such as a superconductive magnet, a normal conductive magnet, or the like that is immersed in cooling liquid (e.g., liquid helium) filling the vacuum container. The static magnetic field magnet 1 is thus configured to generate the static magnetic field in the space on the inside of the vacuum container.

The gradient coil 2 is formed to have a hollow and substantially circular cylindrical shape (which may have an oval cross-section orthogonal to the central axis thereof) and is disposed on the inside of the static magnetic field magnet 1. The gradient coil 2 includes three coils configured to generate gradient magnetic fields along x-, y-, and z-axes, respectively, that are orthogonal to one another. In this situation, the x-axis, the y-axis, and the z-axis structure an apparatus coordinate system unique to the MRI apparatus 100. For example, the x-axis direction is set in the horizontal direction, whereas the y-axis direction is set in the vertical direction. Further, the z-axis direction is set so as to be the same as the direction of a magnetic flux in the static magnetic field generated by the static magnetic field magnet 1.

By individually supplying an electric current to each of the three coils included in the gradient coil 2, the gradient power source 3 is configured to cause the gradient magnetic fields to be generated along the x-, y-, and z-axes, respectively, in the space formed on the inside. The gradient power source 3 is able to cause the gradient magnetic fields to be generated along a read-out direction, a phase-encoding direction, and a slice direction that are orthogonal to each other by generating the gradient magnetic fields along the x-, y-, and z-axes, as appropriate.

In this situation, the axes extending along the read-out direction, the phase-encoding direction, and the slice direction structure a logical coordinate system used for defining slice regions or a volume region serving as a target of an image taking process. In the following sections, the gradient magnetic field generated along the read-out direction will be referred to as a read-out gradient magnetic field; the gradient magnetic field generated along the phase-encoding direction will be referred to as a phase-encoding gradient magnetic field; and the gradient magnetic field generated along the slice direction will be referred to as a slice gradient magnetic field.

Further, the gradient magnetic fields are superimposed on the static magnetic field generated by the static magnetic field magnet 1 and are used for appending spatial position information to magnetic resonance (MR) signals. More specifically, the read-out gradient magnetic field appends position information along the read-out direction to an MR signal, by varying the frequency of the MR signal in accordance with the position in the read-out direction. Further, the phase-encoding gradient magnetic field appends position information in the phase-encoding direction to an MR signal, by varying the phase of the MR signal along the phase-encoding direction. Further, when an image taking region is represented by slice regions, the slice gradient magnetic field is used for determining the orientations, the thicknesses, and the quantity of the slice regions. In contrast, when the image taking region is represented by a volume region, the slice gradient magnetic field appends position information along the slice direction to an MR signal, by varying the phase of the MR signal in accordance with the position in the slice direction.

The transmission coil 4 is configured to apply a radio frequency magnetic field to the space on the inside thereof. More specifically, the transmission coil 4 is formed to have a hollow and substantially circular cylindrical shape (which may have an oval cross-section orthogonal to the central axis thereof) and is disposed on the inside of the gradient coil 2. Further, on the basis of a Radio Frequency (RF) pulse output from the transmitter circuitry 5, the transmitter coil 4 is configured to apply the radio frequency magnetic field to the space on the inside thereof.

The transmitter circuitry 5 is configured to output the radio frequency pulse corresponding to a Larmor frequency to the transmitter coil 4. For example, the transmitter circuitry 5 includes an oscillation circuit, a phase selecting circuit, a frequency converting circuit, an amplitude modulating circuit, and a radio frequency amplifying circuit. The oscillation circuit is configured to generate the radio frequency pulse having a resonant frequency unique to a targeted atomic nucleus placed in the static magnetic field. The phase selecting circuit is configured to select a phase of the radio frequency pulse output from the oscillation circuit. The frequency converting circuit is configured to convert the frequency of the radio frequency pulse output from the phase selecting circuit. The amplitude modulating circuit is configured to modulate the amplitude of the radio frequency pulse output from the frequency converting circuit, according to a sinc function, for example. The radio frequency amplifying circuit is configured to amplify the radio frequency pulse output from the amplitude modulating circuit and to output the amplified radio frequency pulse to the transmitter coil 4.

The receiver coil 6 is configured to receive MR signals emitted from a subject S. For example, the receiver coil 6 is attached to the subject S placed on the inside of the transmitter coil 4 and is configured to receive the MR signals emitted from the subject S due to an influence of the radio frequency magnetic fields applied by the transmitter coil 4. Further, the receiver coil 6 is configured to output the received MR signals to the receiver circuitry 7. For example, as the receiver coil 6, a coil dedicated for each of the various sites serving as targets of image taking processes is used. In this situation, examples of the coils dedicated for the various sites include a receiver coil for the head, a receiver coil for the neck, a receiver coil for a shoulder, a receiver coil for the chest, a receiver coil for the abdomen, a receiver coil for a leg, and a receiver coil for the spine.

The receiver circuitry 7 is configured to generate MR signal data on the basis of the MR signals output from the receiver coil 6 and to output the generated MR signal data to the processing circuitry 14. For example, the receiver circuitry 7 includes a selecting circuit, a pre-amplifying circuit, a phase detecting circuit, and an analog digital converting circuit. The selecting circuit is configured to selectively receive an input of the MR signals output from the receiver coil 6. The pre-amplifying circuit is configured to amplify the MR signals output from the selecting circuit. The phase detecting circuit is configured to detect the phases of the MR signals output from the pre-amplifying circuit. The analog digital converting circuit is configured to generate the MR signal data by converting analog signals output from the phase detecting circuit into digital signals and to output the generated MR signal data to the processing circuitry 14.

In the present example, the situation in which the transmitter coil 4 applies the radio frequency magnetic field so that the receiver coil 6 receives the MR signals is explained; however, possible embodiments of the radio frequency coils are not limited to this example. For instance, the transmitter coil 4 may further have a receiving function to receive the MR signals. Further, the receiver coil 6 may further have a transmitting function to apply the radio frequency magnetic field. When the transmitter coil 4 has the receiving function, the receiver circuitry 7 generates MR signal data also from the MR signals received by the transmitter coil 4. Further, when the receiver coil 6 has the transmitting function, the transmitter circuitry 5 outputs a radio frequency pulse also to the receiver coil 6.

The gantry 8 houses therein the static magnetic field magnet 1, the gradient coil 2, and the transmitter coil 4. More specifically, the gantry 8 has a bore B that is hollow and is formed to have a circular cylindrical shape. While the static magnetic field magnet 1, the gradient coil 2, and the transmitter coil 4 are disposed so as to surround the bore B, the gantry 8 supports the static magnetic field magnet 1, the gradient coil 2, and the transmitter coil 4. In this situation, the space on the inside of the bore B of the gantry 8 corresponds to an image taking space in which the subject S is placed when an image taking process is performed on the subject S.

The couch 9 includes a couchtop 9a on which the subject S is placed. When an image taking process is performed on the subject S, the couchtop 9a is inserted to the inside of the bore B of the gantry 8. For example, the couch 9 is installed in such a manner that the longitudinal direction thereof extends parallel to the central axis of the static magnetic field magnet 1.

The input circuitry 10 is configured to receive operations to input various types of instructions and various types of information from the operator. More specifically, the input circuitry 10 is connected to the processing circuitry 16 and is configured to convert the input operations received from the operator into electrical signals and to output the electrical signals to the processing circuitry 16. For example, the input circuitry 10 is realized with a trackball, a switch button, a mouse, a keyboard, a touch panel, and/or the like.

The display 11 is configured to display various types of information and various types of images. More specifically, the display 11 is connected to the processing circuitry 16 and is configured to convert the various types of information and data of the various types of images sent thereto from the processing circuitry 16, into display-purpose electrical signals and to output the display-purpose electrical signals. For example, the display 11 is realized with a liquid crystal monitor, a Cathode Ray Tube (CRT) monitor, a touch panel, or the like.

The storage circuitry 12 is configured to store various types of data therein. More specifically, the storage circuitry 12 is configured to store therein the MR signal data and image data for each subject S. For example, the storage circuitry 12 is realized with a semiconductor memory device such as a Random Access Memory (RAM), a flash memory, or the like, or a hard disk, an optical disk, or the like.

The processing circuitry 13 includes a couch controlling function 13a. For example, the processing circuitry 13 is realized with a processor. The couch controlling function 13a is connected to the couch 9 and is configured to control operations of the couch 9 by outputting a control-purpose electrical signal to the couch 9. For example, the couch controlling function 13a receives, via the input circuitry 10, an instruction to move the couchtop 9a in a longitudinal direction, an up-and-down direction, or a left-and-right direction from the operator and operates a driving mechanism for the couchtop 9a included in the couch 9 so as to move the couchtop 9a according to the received instruction.

The processing circuitry 14 includes an executing function 14a. For example, the processing circuitry 14 is realized with a processor. The executing function 14a is configured to perform a data acquisition to acquire the MR signal data by driving the gradient power source 3, the transmitter circuitry 5, and the receiver circuitry 7, on the basis of sequence execution data output from the processing circuitry 16.

In this situation, the sequence execution data is information that defines a pulse sequence indicating a procedure performed to acquire the MR signal data. More specifically, the sequence execution data is information that defines: the timing with which the electric current is to be supplied from the gradient power source 3 to the gradient coil 2 and the intensity of the electric current to be supplied; the intensity of the radio frequency pulse to be supplied from the transmitter circuitry 5 to the transmitter coil 4 and the timing with which the radio frequency pulse is to be supplied; the timing with which the MR signals are to be detected by the receiver circuitry 7, and the like.

Further, the executing function 14a is configured to receive the MR signal data from the receiver circuitry 7 as a result of executing various types of pulse sequences and to store the received MR signal data into the storage circuitry 12. A set made up of pieces of MR signal data received by the executing function 14a is stored in the storage circuitry 12 as data structuring a k-space as a result of being arranged two-dimensionally or three-dimensionally according to the position information appended by the read-out gradient magnetic field, the phase-encoding gradient magnetic field, and the slice gradient magnetic field described above.

The processing circuitry 15 includes an image generating function 15a. For example, the processing circuitry 15 is realized with a processor. The image generating function 15a is configured to generate an image on the basis of the MR signal data stored in the storage circuitry 12. More specifically, the image generating function 15a generates the image by reading the MR signal data stored into the storage circuitry 12 by the executing function 14a and further performing a reconstructing process such as a post-processing process (i.e., a Fourier transform or the like) on the read MR signal data. Further, the image generating function 15a stores image data of the generated image into the storage circuitry 12.

The processing circuitry 16 is configured to exercise overall control of the MRI apparatus 100 by controlling constituent elements of the MRI apparatus 100. For example, the processing circuitry 16 is realized with a processor. For example, the processing circuitry 16 receives an image taking condition (e.g., an input of various types of parameters related to the pulse sequence) from the operator via the input circuitry 10 and generates the sequence execution data on the basis of the received image taking condition. After that, the processing circuitry 16 controls the data acquisition to acquire the MR signal data, by transmitting the generated sequence execution data to the processing circuitry 14. Further, for example, the processing circuitry 16 reads the image data of an image requested by the operator from the storage circuitry 12 and outputs the read image to the display 11.

The ECG sensor 17 is attached to the body surface of the subject S and is configured to detect an electrocardiographic signal of the subject S. After that, the ECG sensor 17 outputs the detected electrocardiographic signal to the ECG circuitry 18.

The ECG circuitry 18 is configured to detect a predetermined electrocardiographic waveform on the basis of the electrocardiographic signal output from the ECG sensor 17. For example, the ECG circuitry 18 is configured to detect an R-wave as the predetermined electrocardiographic waveform. After that, the ECG circuitry 18 generates a trigger signal at the time when the predetermined electrocardiographic waveform is detected and outputs the generated trigger signal to the processing circuitry 16.

A configuration of the MRI apparatus 100 according to the first embodiment has thus been explained. The MRI apparatus 100 according to the first embodiment configured as described above has a function of performing a synchronization imaging to acquire data of the subject in synchronization with heartbeats.

For example, when a coronary artery Magnetic Resonance Angiography (MRA) is implemented, generally speaking, the timing with which a data acquisition is performed (hereinafter, "data acquisition timing") is set within a cardiac rest period (coronary artery rest periods) corresponding to a diastolic period during which the movements of the ventricles are smallest. The data acquisition timing is a parameter that is set in advance before the synchronization imaging performed on the subject is started. The data acquisition timing is set to a time that is later than an R-wave in the electrocardiogram by a predetermined time period.

However, when the data acquisition timing is set in this manner to the time that is later than the R-wave by the predetermined time period, there is a possibility that image quality may be degraded by fluctuation of the heartbeats of the subject. For example, during the synchronization imaging, when the heart of the subject experiences an extrasystole due to a physiological impact or the like, the RR interval in the cardiac cycle changes. As a result, the data acquisition timing may fall outside of the cardiac rest period. In that situation, there is a possibility that the image quality may be degraded. Further, physiological factors that may cause such fluctuation of heartbeats usually vary among subjects.

Further, there are roughly three types of cardiac rest periods in cardiac cycles. One is diastasis period, which is usually the longest rest period in a cardiac cycle that typically lasts approximately 100 ms to 300 ms in mesodiastole. The other types of cardiac rest periods are a cardiac rest period that lasts approximately 50 ms to 60 ms corresponding to isovolumic relaxation in end-systole and a cardiac rest period that lasts approximately 30 ms corresponding to isovolumic contraction in end-diastole. These cardiac rest periods in cardiac cycles tend to vary among individuals and depending on heart rates.

Consequently, the MRI apparatus 100 according to the first embodiment is configured to be able to perform an image taking process on each subject with appropriate timing corresponding to fluctuation of subject-specific heartbeats.

More specifically, the MRI apparatus 100 according to the first embodiment is configured to derive data acquisition timing in the synchronization imaging by using a subject-specific regression model that indicates a relationship among a cardiac cycle, systole, and diastole of the subject and to further perform a data acquisition by using the derived timing.

To realize such a configuration, in the first embodiment, the processing circuitry 16 includes a first deriving function 16a, a second deriving function 16b, and a controlling function 16c. The first deriving function 16a is an example of the first deriving unit. The second deriving function 16b is an example of the second deriving unit. The controlling function 16c is an example of the controlling unit.

The first deriving function 16a is configured to derive the subject-specific regression model that indicates a relationship among the cardiac cycle, systole, and diastole of the subject. In this situation, for example, the relationship among the cardiac cycle, systole, and diastole is related to a boundary between the systole and the diastole. Further, for example, the boundary between the systole and the diastole may be represented by a T-wave in an electrocardiographic waveform.

More specifically, as the subject-specific regression model, the first deriving function 16a is configured to derive a mathematical function expressing a relationship between an RR interval and a QT interval in the electrocardiographic waveform. In this situation, the RR interval is a time interval from the R-wave in one heartbeat to the R-wave in the following heartbeat. Further, the QT interval is a time interval from the Q-wave to the T-wave in one heartbeat.

For example, the first deriving function 16a derives the regression model indicating the relationship with the boundary between systole and diastole, on the basis of electrocardiographic information in a predetermined time period (e.g., 24 hours) acquired from the subject by using a Holter electrocardiograph. In this situation, the Holter electrocardiograph is a small electrocardiograph that can be carried around by the subject. For example, the Holter electrocardiograph makes it possible to acquire electrocardiographic information for a long period of time from the subject in a daily life.

Figure 2:
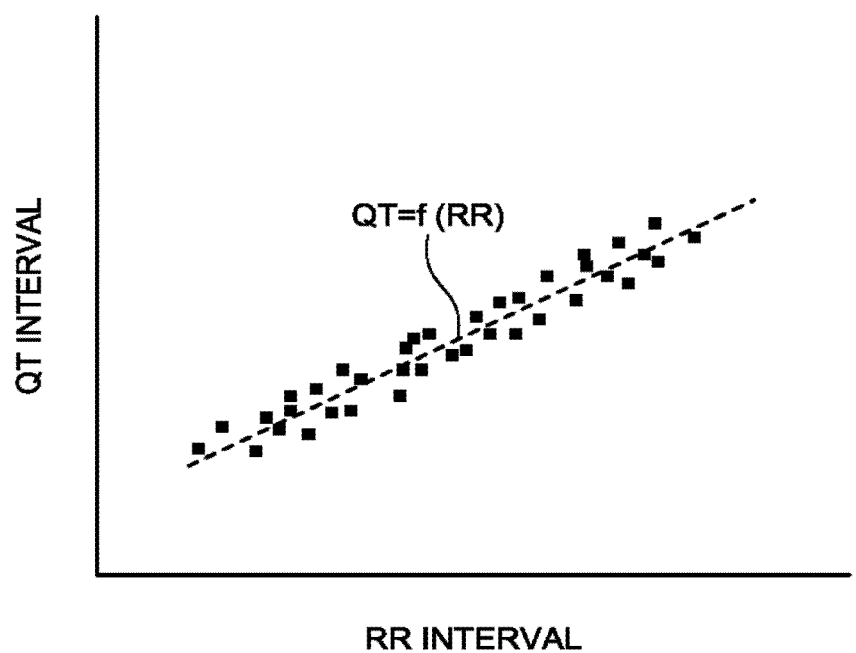
FIG. 2 is a chart illustrating an example of a regression model generating process performed by a first deriving function according to the first embodiment.

FIG. 2 is a chart illustrating an example of a regression model generating process performed by the first deriving function 16a according to the first embodiment. FIG. 2 illustrates a distribution of values of the RR interval and the QT interval for each of the heartbeats included in the electrocardiographic information in the predetermined time period acquired from the subject by using the Holter electrocardiograph.

For example, as indicated in FIG. 2 with the broken line, the first deriving function 16a derives, as the subject-specific regression model, a relational expression (a regression expression) indicating a relationship between the RR interval and the QT interval, by performing a regression analysis while using the electrocardiographic information in the predetermined time period acquired by the Holter electrocardiograph. The relational expression derived in this situation may be expressed with a linear function or may be expressed with a non-linear function such as a logarithmic function or an exponential function.

For example, when the RR interval corresponding to one heartbeat is expressed as RR, while the QT interval is expressed as QT, the regression model derived by the first deriving function 16a can be expressed by using Expression (1) presented below.

$$QT = f(RR) \quad (1)$$

In this situation, as explained above, because the physiological factors that cause fluctuation of heartbeats vary among subjects, the distribution illustrated in FIG. 2 also varies among subjects. Accordingly, the regression model derived by the first deriving function 16a also varies among subjects.

Returning to the description of FIG. 1, the second deriving function 16b is configured to derive data acquisition timing in the synchronization imaging performed in synchronization with heartbeats, by using the regression model derived by the first deriving function 16a and the electrocardiographic information of the subject obtained during the image taking process. In this situation, the data acquisition timing is defined with an elapsed time period since the R-wave.

More specifically, the second deriving function 16b detects the occurrence of an R-wave from a trigger signal output from the ECG circuitry 18. After that, every time the occurrence of an R-wave is detected, the second deriving function 16b derives data acquisition timing in the synchronization imaging and notifies the controlling function 16c of an elapsed time period indicating the derived timing.

In this situation, with respect to the first heartbeat in the synchronization imaging, the second deriving function 16b is configured to determine a stationary phase of the heart of the subject by using the data obtained on a stage prior to the synchronization imaging and to derive the data acquisition timing by using the determined stationary phase and the regression model derived by the first deriving function 16a. In other words, with respect to the first heartbeat, the second deriving function 16b estimates the data acquisition timing to be used in the synchronization imaging performed for the first time, by using the stationary phase determined from the data obtained on the stage prior to the synchronization imaging and the regression model.

Further, with respect to each of the second and later heartbeats in the synchronization imaging, the second deriving function 16b is configured to derive the RR interval from the immediately-preceding R-wave to the present R-wave and to derive data acquisition timing by using the derived RR interval, the data acquisition timing calculated with respect to the immediately-preceding heartbeat, and the regression model derived by the first deriving function 16a. In other words, with respect to each of the second and later heartbeats, the second deriving function 16b estimates the data acquisition timing to be used for the present synchronization imaging, by using the RR interval from the immediately-preceding R-wave to the present R-wave, the immediately-preceding data acquisition timing, and the regression model.

Figure 3:
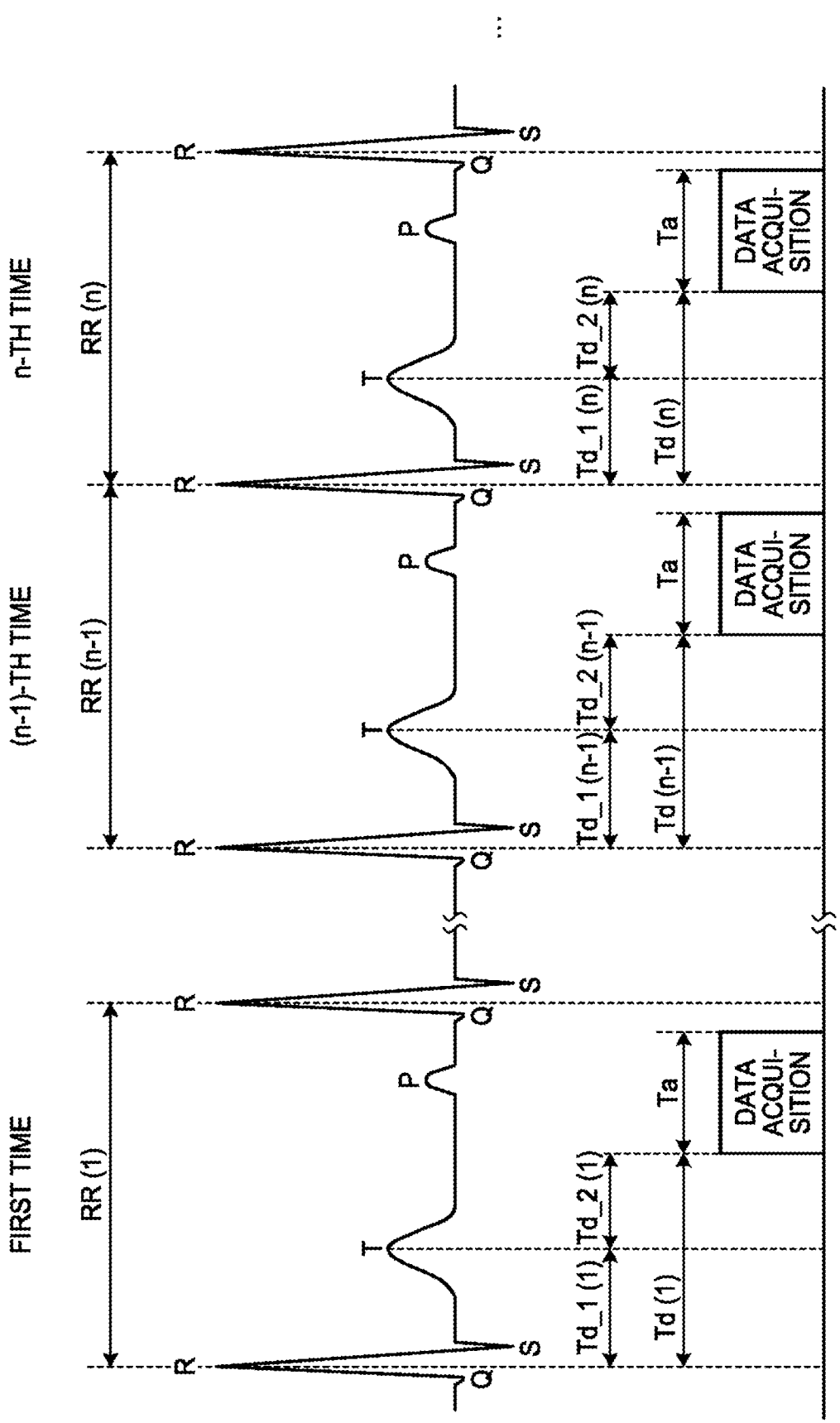
FIG. 3 is a chart illustrating an example of a data acquisition timing deriving process performed by a second deriving function according to the first embodiment.

FIG. 3 is a chart illustrating an example of the data acquisition timing deriving process performed by the second deriving function 16b according to the first embodiment. For example, as illustrated in FIG. 3, with respect to an n-th heartbeat, the RR interval from the immediately-preceding R-wave to the present R-wave is expressed as RR(n−1). Further, the time period from the present R-wave to the present T-wave is expressed as Td_1(n). The time period from the T-wave to the start of the data acquisition is expressed as Td_2(n). Further, the time period totaling Td_1(n) and Td_2(n) is expressed as an elapsed time period Td(n) since the R-wave, which indicates the data acquisition timing for the present time.

In this situation, generally speaking, because the time period from a Q-wave to an R-wave is an extremely short period of time, it is possible to consider the time period Td_1(n) from the R-wave to a T-wave to be equal to the QT interval QT(n), which is the time period from the Q-wave to the T-wave. Accordingly, as indicated in Expression (2) presented below, the second deriving function 16b derives QT(n) from the RR interval by using the regression model derived by the first deriving function 16a and determines the derived value of QT(n) to be Td_1(n).

$$Td\_1(n)=QT(n)=f(RR) \qquad (2)$$

More specifically, with respect to the first heartbeat (where n=1), as indicated in Expression (3) presented below, the second deriving function 16b derives Td_1(1) from the RR interval RR0 in the electrocardiographic information acquired from the subject prior to the medical examination, by using the regression model derived by the first deriving function 16a. In other words, the second deriving function 16b estimates Td_1(1) from the actual measured value RR0, by using the regression model. In this situation, RR0 may be an average value of RR intervals obtained from a plurality of heartbeats.

$$Td\_1(1)=QT(1)=f(RR0) \qquad (3)$$

Further, with respect to the first heartbeat, as indicated in Expression (4) presented below, the second deriving function 16b determines a time period Ts from the T-wave to the stationary phase specified by using a four-chamber image of the heart acquired through cine imaging, to be Td_2(1). In other words, the second deriving function 16b estimates Td_2(1) from the actual measured value Ts. In this situation, the time period Ts may be an average value of time periods from a T-wave to a stationary phase that are obtained from a plurality of heartbeats.

$$Td\_2(1)=Ts \qquad (4)$$

For example, the second deriving function 16b determines the stationary phase by using Magnetic Resonance (MR) images acquired through a cine imaging to obtain four-chamber images of the heart performed on a stage prior to the synchronization imaging.

Figure 4:
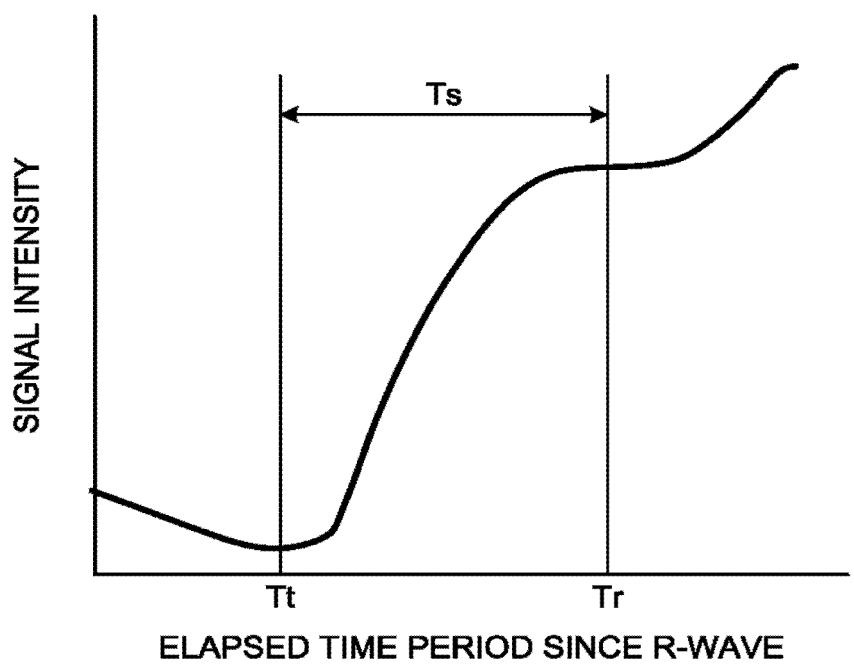
FIG. 4 is a chart illustrating an example of a stationary phase determining process performed by the second deriving function according to the first embodiment.

FIG. 4 is a chart illustrating an example of a stationary phase determining process performed by the second deriving function 16b according to the first embodiment. FIG. 4 illustrates a chronological change, corresponding to one heartbeat, in the signal intensity in the four-chamber images (which hereinafter may be referred to as "cross-sectional images") of the heart acquired through the cine imaging performed on a stage prior to the synchronization imaging. In FIG. 4, the horizontal axis expresses an elapsed time period since the R-wave based on electrocardiographic information acquired from the subject at the same time as the cine imaging. Further, the vertical axis expresses the signal intensity in a region of interest that is set to include a coronary artery, with respect to the cross-sectional images corresponding to multiple temporal phases and having been acquired through the cine imaging. In this situation, the coronary artery may be either the right coronary artery or the left coronary artery.

For example, as illustrated in FIG. 4, by using the cross-sectional images corresponding to the multiple temporal phases, the second deriving function 16b derives, for each of the temporal phases, a change amount in the signal intensity within the region of interest compared to the signal intensity in the immediately-preceding temporal phase. The second deriving function 16b further specifies a temporal phase Tr in which the change amount in the signal intensity is the smallest, the temporal phase Tr being later than a temporal phase Tt corresponding to the T-wave. After that, the second deriving function 16b derives the time period from Tt to Tr, as the time period Ts from the T-wave to the stationary phase.

In the present example, the situation is explained in which the second deriving function 16b automatically specifies the stationary phase; however, possible methods for specifying the stationary phase are not limited to this example. For instance, the second deriving function 16b may cause the display 11 to display the four-chamber images corresponding to multiple temporal phases acquired through the cine imaging and may receive, from the operator, an operation to select one of the four-chamber images judged to have small cardiac movements. In that situation, the second deriving function 16b specifies the temporal phase of the four-chamber image selected by the operator, as the stationary phase.

In the above example, the situation is explained in which the stationary phase is determined by using the MR images obtained by performing the cine imaging to obtain the four-chamber images of the heart; however, possible methods for determining the stationary phase are not limited to this example. For instance, another method is also acceptable in which a correlation coefficient between frames is calculated by using images of the entire heart or images acquired by using only the coronary artery as a region of interest, so as to specify a frame of which the correlation coefficient exceeds a predetermined threshold value as the stationary phase. Alternatively, for example, the second deriving function 16b may determine the stationary phase by using a measurement result obtained from the subject by performing a medical examination while using an ultrasound diagnosis apparatus. In that situation, before the synchronization imaging is performed, the measurement result acquired by the ultrasound diagnosis apparatus is obtained in advance and stored into the storage circuitry 12.

Further, with respect to the first heartbeat, as indicated in Expression (5) presented below, the second deriving function 16b derives an elapsed time period Td(1) since the R-wave that indicates the data acquisition timing for the first time, by adding together Td_1(1) and Td_2(1) that were derived. In other words, the second deriving function 16b estimates Td(1) by using Td_1(1) and Td_2(1) that were estimated from the actual measured values.

$$Td(1)=Td\_1(1)+Td\_2(1) \quad (5)$$

Further, with respect to each of the second and later heartbeats (where n≥2), as indicated in Expression (6) presented below, the second deriving function 16b derives Td_1(n) from the RR interval RR(n−1) from the immediately-preceding R-wave to the present R-wave, by using the regression model derived by the first deriving function 16a. In other words, by using the regression model, the second deriving function 16b estimates Td_1(1) and QT(n) from the actual measured value RR(n−1).

$$Td\_1(n)=QT(n)=f(RR(n-1)) \quad (6)$$

Further, with respect to each of the second and later heartbeats, as indicated in Expression (7) presented below, the second deriving function 16b derives Td_2(n) from the interval RR(n−1) from the immediately-preceding R-wave to the present R-wave, the present QT interval QT(n), and a correction term k, by using the regression model derived by the first deriving function 16a. In other words, by using a regression model, the second deriving function 16b estimates Td_2(n) from the actual measured value RR(n−1) and QT(n) estimated from the actual measured value. Similarly to the regression model indicated in Expression (1), the regression model f used in this situation is a regression model that is obtained by performing a regression analysis while using electrocardiographic information acquired by a Holter electrocardiograph and that indicates a relationship among the RR interval, the QT interval, and the TQ interval. Further, the symbol k denotes a term used for correcting the timing of the stationary phase with respect to the TQ interval TQ(n) predicted for the present time. For example, as indicated in Expression (8) presented below, the term k is calculated from an initial value TQ0 of the TQ interval and the TQ interval TQ(n−1) from the immediately-preceding T-Wave to the immediately-preceding Q-wave. Similarly to Ts, TQ0 used in this situation is, for example, the time period from the T-wave to the Q-wave specified by using the four-chamber images of the heart acquired by performing the cine imaging. Alternatively, TQ0 may be an average value of TQ intervals obtained from a plurality of heartbeats.

$$Td\_2(n)=TQ(n)\times k=f(RR(n-1),QT(n))\times k \quad (7)$$

$$k=Ts\times TQ0/TQ(n-1) \quad (8)$$

Further, with respect to each of the second and later heartbeats, as indicated in Expression (9) presented below, the second deriving function 16b derives an elapsed time period Td(n) since the R-wave that indicates the n-th data acquisition timing, by adding together Td_1(n) and Td_2(n) that were derived. In other words, the second deriving function 16b estimates Td(n) by using Td_1(n) and Td_2(n) estimated from the actual measure values.

$$Td(n)=Td\_1(n)+Td\_2(n) \quad (9)$$

In this manner, with respect to each of the second and later heartbeats, the data acquisition timing is derived during the image taking process in a real-time manner, in accordance with the actual measured RR interval and the immediately-preceding data acquisition timing.

In the above description, the example is explained in which the second deriving function 16b determines the stationary phase of the heart by using the data obtained on the stage prior to the synchronization imaging; however, possible embodiments are not limited to this example. For instance, the second deriving function 16b may determine a stationary phase of the heart of the subject while the synchronization imaging is being performed, so as to derive data acquisition timing by using the determined stationary phase and the regression model. As a method for determining the stationary phase while the synchronization imaging is being performed, it is acceptable to use any of various types of publicly-known methods such as a method by which a stationary phase is determined by using the interventricular septum, for example.

Returning to the description of FIG. 1, the controlling function 16c controls the synchronization imaging so that the data acquisitions are performed with the timing derived by the second deriving function 16b. More specifically, every time an elapsed time period indicating data acquisition timing is provided as a notification from the second deriving function 16b, the controlling function 16c transmits, to the processing circuitry 14, sequence execution data generated on the basis of the image taking condition, at the point in time when the elapsed time period has elapsed since the time at which the notification was provided. In this situation, in the first embodiment, the controlling function 16c generates the sequence execution data so that the data is acquired during a data acquisition time period Ta (see FIG. 3) that is set in advance as the image taking condition. In this situation, the data acquisition time period is a time period during which the data is acquired. With these arrangements, the data acquisition to acquire MR signal data is performed at the point in time when the elapsed time period derived by the second deriving function 16b has elapsed since the point in time at which the R-wave was detected.

Further, for example, when coronary artery MRA is implemented, generally speaking, in many situations, a pre-pulse (e.g., a fat suppression pulse, a movement correction RF pulse, or the like) is applied prior to a data acquisition pulse sequence used for obtaining images. For this reason, for example, when such a pre-pulse is applied prior to the data acquisition in the synchronization imaging, the controlling function 16c may transmit the sequence execution data to the processing circuitry 14 at a time that is earlier by the application time period of the pre-pulse, so that the application of the pre-pulse is completed before the data acquisition timing derived by the second deriving function 16b.

The processing functions of the pieces of processing circuitry 13 to 16 have thus been explained. For example, these processing functions are stored in the storage circuitry 12 in the form of computer-executable programs. By reading a corresponding one of the programs from the storage circuitry 12 and executing the read program, each of the pieces of processing circuitry realizes the processing function corresponding to the program. In other words, each of the pieces of processing circuitry 13 to 16 that has read the corresponding program has the corresponding one of the processing functions illustrated in FIG. 1.

Further, in the example illustrated in FIG. 1, the processing functions of the pieces of processing circuitry are each realized by a single piece of processing circuitry; however, possible embodiments are not limited to this example. Any of the processing functions of the pieces of processing circuitry may be realized as being distributed to a plurality of pieces of processing circuitry or being integrated into a single piece of processing circuitry.

Figure 5:
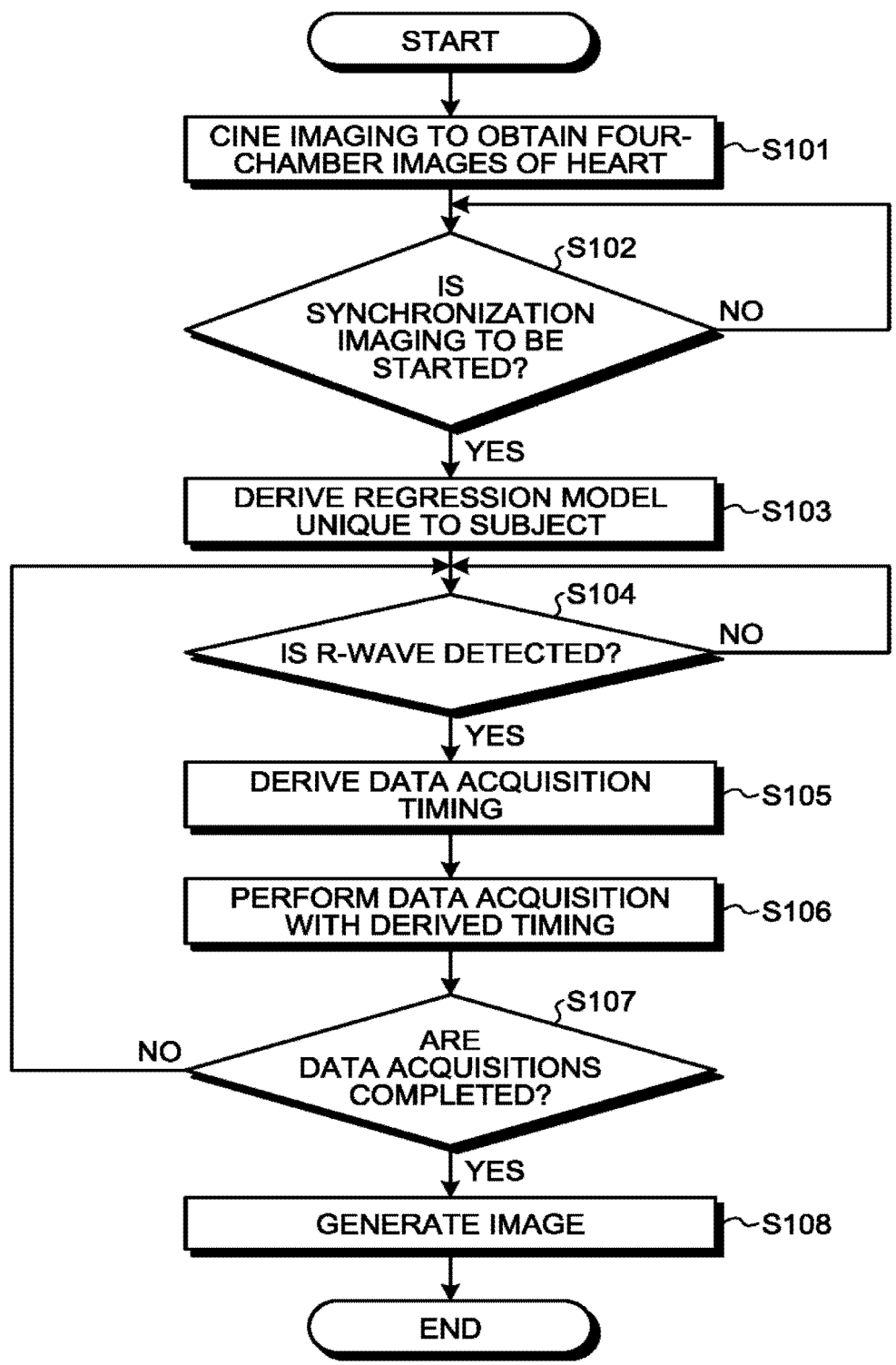
FIG. 5 is a flowchart illustrating a processing procedure in a synchronization imaging performed by the MRI apparatus according to the first embodiment.

FIG. 5 is a flowchart illustrating a processing procedure in the synchronization imaging performed by the MRI apparatus 100 according to the first embodiment. For example, as illustrated in FIG. 5, in the first embodiment, the controlling function 16c performs a cine imaging to obtain four-chamber images of the heart (step S101). The cine imaging may be performed as a part of a pre-scan performed prior to a main scan including the synchronization imaging or may be performed by itself prior to the main scan, separately from the pre-scan.

After that, when having received an instruction from the operator via the input circuitry 10 indicating that the synchronization imaging be started (step S102: Yes), the first deriving function 16a derives a subject-specific regression model that indicates a relationship among the cardiac cycle, systole, and diastole of the subject (step S103).

Subsequently, when an R-wave is detected via the ECG circuitry 18 (step S104: Yes), the second deriving function 16b derives data acquisition timing in the synchronization imaging to be performed in synchronization with heartbeats, by using the regression model derived by the first deriving function 16a and the electrocardiographic information of the subject obtained in a real-time manner (step S105).

After that, the controlling function 16c performs a data acquisition with the timing derived by the second deriving function 16b (step S106).

In this situation, until all the data acquisitions are completed (step S107: No), the processes at steps S104 through S107 described above are repeatedly performed. Further, when all the data acquisitions are completed (step S107: Yes), the image generating function 15a generates an image of the subject on the basis of the acquired MR signal data (step S108).

With the processing procedure described above, in the synchronization imaging, every time an R-wave is detected, the data acquisition timing is derived during the image taking process by using the subject-specific regression model in a real-time manner, so as to perform the data acquisitions.

In the processing procedure described above, the processes at steps S101 and S106 are realized, for example, as a result of the processing circuitry 16 invoking and executing a predetermined program corresponding to the controlling function 16c from the storage circuitry 12. The processes at steps S102 and S103 are realized, for example, as a result of the processing circuitry 16 invoking and executing a predetermined program corresponding to the first deriving function 16a from the storage circuitry 12. The processes at steps S104 and S105 are realized, for example, as a result of the processing circuitry 16 invoking and executing a predetermined program corresponding to the second deriving function 16b from the storage circuitry 12. The processes at steps S107 and S108 are realized, for example, as a result of the processing circuitry 15 invoking and executing a predetermined program corresponding to the image generating function 15a from the storage circuitry 12.

As explained above, the MRI apparatus 100 according to the first embodiment is configured to derive the data acquisition timing in the synchronization imaging by using the subject-specific regression model that indicates the relationship among the cardiac cycle, systole, and diastole of the subject and configured to perform the data acquisitions with the derived timing. Consequently, according to the first embodiment, it is possible to perform the image taking process on the subject with the appropriate timing corresponding to the fluctuation of subject-specific heartbeats. As a result, it is possible to improve the degradation in image quality that may be caused by the fluctuation of heartbeats and to provide an image having a high level of diagnosis capability. Further, it is possible to reduce the possibility that the image taking process needs to be performed again due to the degradation of image quality. It is therefore possible to make contribution to reducing the burden on the subject himself/herself who is examined.

In the embodiment described above, the example is explained in which the first deriving function 16a derives the mathematical function expressing the relationship between the RR interval and the QT interval in the electrocardiographic waveform, as the subject-specific regression model that indicates the relationship among the cardiac cycle, systole, and diastole; however, possible methods for deriving the regression model are not limited to this example.

For instance, as a subject-specific regression model, the first deriving function 16a may derive a mathematical function expressing a relationship between the RR interval and the TR interval in an electrocardiographic waveform. In that situation, as the subject-specific regression model, the first deriving function 16a derives a relational expression indicating the relationship between the RR interval and the TR interval, by performing a regression analysis while using electrocardiographic information in a predetermined time period acquired by a Holter electrocardiograph. The relational expression derived in this situation may be expressed with a linear function or may be expressed with a non-linear function such as a logarithmic function or an exponential function.

For example, when the RR interval corresponding to one heartbeat is expressed as RR, while the TR interval is expressed as TR, the regression model derived by the first deriving function 16a can be expressed by using Expression (11) presented below.

$$TR = f(RR) \tag{11}$$

Further, in that situation, with respect to an n-th heartbeat, as indicated in Expression (12) presented below, the second deriving function 16b derives TR(n) from the RR interval RR(n−1) from the immediately-preceding R-wave to the present R-wave, by using the regression model derived by the first deriving function 16a. In other words, the second deriving function 16b estimates TR(n) from the actual measured value RR(n−1), by using the regression model. Further, as indicated in Expression (13) presented below, the second deriving function 16b considers the RR interval RR(n) from the present R-wave to the immediately-following R-wave to be equal to the RR interval RR(n−1) from the immediately-preceding R-wave to the present R-wave and derives RT(n) by subtracting TR(n) from RR(n−1). After that, as indicated in Expression (14), the second deriving function 16b determines the derived value of RT(n) to be Td_1(n). In other words, the second deriving function 16b estimates Td_1(n) by using the actual measured value RR(n−1) and TR(n) estimated from the actual measured value.

$$TR(n) = f(RR(n-1)) \tag{12}$$

$$RT(n) = RR(n) - TR(n) \tag{13}$$
$$= RR(n-1) - TR(n)$$

$$Td\_1(n) = RT(n) \tag{14}$$

After that, in the same manner as in the first embodiment, the second deriving function 16b derives the elapsed time period Td(n) since the R-wave that indicates the data acquisition timing with respect to the n-th heartbeat (where n≥1), by using Expressions (7) to (9).

Alternatively, for example, the first deriving function 16a may derive, as a subject-specific regression model, a mathematical function expressing the TP interval in an electrocardiographic waveform from a relationship between the RR interval and the PT interval in the electrocardiographic waveform. In that situation, as the subject-specific regression model, the first deriving function 16a derives a relational expression expressing the TP interval from the relationship between the RR interval and the PT interval, by performing a regression analysis while using electrocardiographic information in a predetermined time period acquired by a Holter electrocardiograph. For example, when the RR interval corresponding to one heartbeat is expressed as RR, the PT interval is expressed as PT, and the TR interval is expressed as TR, the regression model derived by the first deriving function 16a can be expressed by using Expression (21) presented below.

$$TP=f(RR,PT) \tag{21}$$

In that situation, for example, with respect to an n-th heartbeat, as indicated in Expression (22) presented below, the second deriving function 16b derives the present TP interval TP(n) from the immediately-preceding RR interval RR(n−1) and the immediately-preceding PT interval PT(n−1), by using the regression model derived by the first deriving function 16a. In other words, the second deriving function 16b estimates TP(n) from the actual measured values RR(n−1) and PT(n−1), by using the regression model. Further, as indicated in Expression (23) presented below, the second deriving function 16b derives Td_1(n) from the derived value of TP(n), the immediately-preceding Td_1(n−1), and the immediately-preceding TP(n−1). In other words, the second deriving function 16b estimates Td_1(n) by using the actual measured values Td_1(n−1) and TP(n−1), as well as TP(n) estimated from the other actual measured values.

$$TP(n)=f(RR(n-1),PT(n-1)) \tag{22}$$

$$Td\_1(n)=Td\_1(n-1) \times TP(n)/TP(n-1) \tag{23}$$

After that, in the same manner as in the first embodiment, the second deriving function 16b derives the elapsed time period Td(n) since the R-wave that indicates the data acquisition timing with respect to the n-th heartbeat (where n≥1), by using Expressions (7) to (9).

In yet another example, the first deriving function 16a may derive, as a subject-specific regression model, a mathematical function expressing the TQ interval in an electrocardiographic waveform from a relationship between the RR interval and the QT interval. For example, when the RR interval corresponding to one heartbeat is expressed as RR, the QT interval is expressed as QT, and the TQ interval is expressed as TQ, the regression model derived by the first deriving function 16a can be expressed by using Expression (31) presented below.

$$TQ=f(RR,QT) \tag{31}$$

In that situation, for example, with respect to an n-th heartbeat, as indicated in Expression (32) presented below, the second deriving function 16b derives the present TQ interval TQ(n) from the immediately-preceding RR interval RR(n−1) and the immediately-preceding QT interval QT(n−1), by using the regression model derived by the first deriving function 16a. In other words, the second deriving function 16b estimates TQ(n) from the actual measured values RR(n−1) and QT(n−1) by using the regression model. Further, as indicated in Expression (33) presented below, the second deriving function 16b considers the present RR interval RR(n) to be equal to the immediately-preceding RR interval RR(n−1), also considers the present TQ(n) to be equal to TR(n), and derives RT(n) by subtracting TQ(n) from RR(n−1). Subsequently, as indicated in Expression (34), the second deriving function 16b determines the derived value of RT(n) to be Td_1(n). In other words, the second deriving function 16b estimates Td_1(n) by using the actual measured value RR(n−1) and the value of TQ(n) estimated from the actual measured values.

$$TQ(n)=f(RR(n-1),QT(n-1)) \tag{32}$$

$$RT(n)=RR(n)-TR(n) \tag{33}$$
$$=RR(n-1)-TQ(n)$$

$$Td\_1(n)=RT(n) \tag{34}$$

After that, in the same manner as in the first embodiment, the second deriving function 16b derives the elapsed time period Td(n) since the R-wave that indicates the data acquisition timing with respect to the n-th heartbeat (where n≥1), by using Expressions (7) to (9).

Further, in the first embodiment above, the example is explained in which, during the synchronization imaging, the second deriving function 16b keeps using the regression model derived by the first deriving function 16a; however, possible embodiments are not limited to this example. For instance, the second deriving function 16b may correct the regression model in accordance with a judgment result of the state of the heart of the subject, while the synchronization imaging is being performed.

For example, when a mathematical function expressing a relationship between the RR interval and the QT interval is derived as a regression model by the first deriving function 16a, the second deriving function 16b measures, after the synchronization imaging is started, a QT interval for each of the heartbeats, on the basis of the electrocardiographic signal detected by the ECG sensor 17 and the ECG circuitry 18. After that, for each of the heartbeats, the second deriving function 16b compares the actual measured QT interval with the QT interval derived by using the regression model with respect to the present heartbeat, and when the values are different from each other, corrects one or more coefficients included in the mathematical functions of the regression model so as to be able to obtain a result conforming to the actual measured QT interval.

For example, when the heart rate of the subject is not stable while the synchronization imaging is being performed, medication may be administered to the subject intravenously or in other ways, in some situations. In those situations, although the heart rate of the subject may become stable, the fluctuation of heartbeats of the subject may be in a different state from the state which was observed when the electrocardiographic information was acquired and based on which the regression model was derived by the first deriving function 16a. Even in that situation, by correcting the regression model as described above in accordance with the judgment result of the state of the heart of the subject while the synchronization imaging is being performed, it is possible to perform the data acquisitions with more appropriate timing.

Second Embodiment

In the embodiment described above, the example is explained in which the single regression model is used as the subject-specific regression model; however, possible embodiments are not limited to this example. For instance, when the subject has a heart disease such as atrial fibrillation, arrhythmia, or the like, the state of the heart may change during a medical examination even for the same subject. For example, it is not possible to predict when atrial fibrillation may occur.

To cope with this situation, for example, it is also acceptable to use a plurality of regression models in accordance with multiple states of the heart of the subject. In the following sections, an example will be explained in which a plurality of regression models are used will be explained as a second embodiment. The configuration of an MRI apparatus according to the second embodiment is basically the same as the configuration illustrated in FIG. 1. Accordingly, in the following sections, various functions will be explained while a focus is placed on differences from those explained in the first embodiment.

In the second embodiment, the first deriving function 16a derives, as subject-specific regression models that each indicate a relationship between heartbeats of the subject and a boundary between systole and diastole, a plurality of regression models corresponding to multiple states of the heart of the subject. For example, in the same manner as in the first embodiment, the first deriving function 16a derives the regression models each indicating a relationship with the boundary between systole and diastole, on the basis of electrocardiographic information in a predetermined time period acquired from the subject by using a Holter electrocardiograph.

Figure 6:
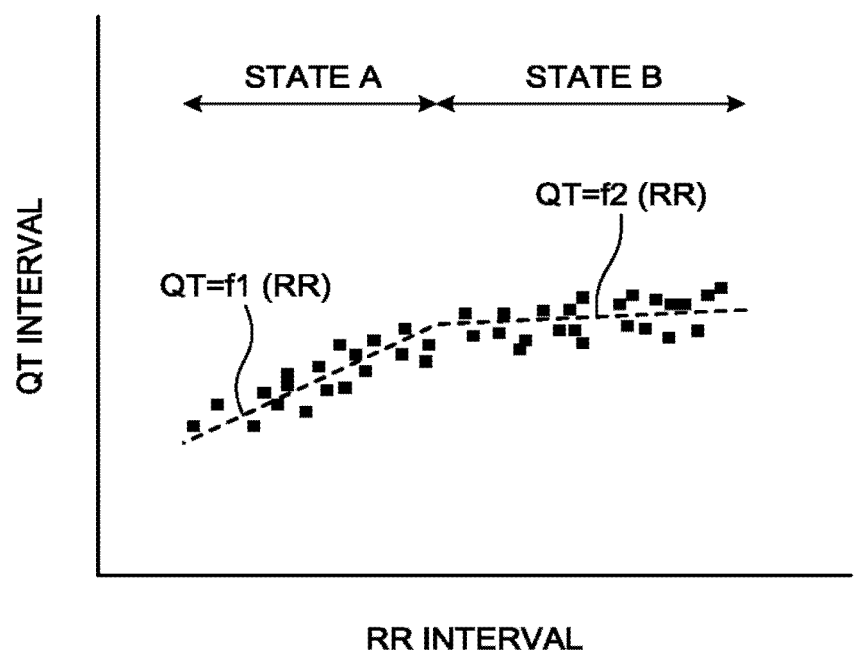
FIG. 6 is a chart illustrating an example of a regression model generating process performed by a first deriving function according to a second embodiment.

FIG. 6 is a chart illustrating an example of a regression model generating process performed by the first deriving function 16a according to the second embodiment. Similarly to the example illustrated in FIG. 2, FIG. 6 illustrates a distribution of values of the RR interval and the QT interval for each of the heartbeats included in the electrocardiographic information in the predetermined time period acquired from the subject by using the Holter electrocardiograph.

For example, as illustrated in FIG. 6, when the subject has a heart disease such as atrial fibrillation, arrhythmia, or the like, the tendency of the distribution of values of the RR interval and the QT interval for each of the heartbeats may vary among mutually-different ranges of RR interval values, even for the same subject, depending on the state of the heart of the subject. FIG. 6 illustrates an example in which the state of the heart of the subject changes between two states such as state A and state B corresponding to two ranges of RR interval values. For example, state A is a state in which the heart is moving with a normal sinus rhythm, whereas state B is a state in which arrhythmia (e.g., bradycardia arrhythmia) is occurring.

In that situation, for example, the first deriving function 16a derives, as subject-specific regression models, a plurality of relational expressions each indicating a relationship between an RR interval and a QT interval and corresponding to a different one of the multiple states of the heart of the subject, by performing a regression analysis while using the electrocardiographic information in the predetermined time period acquired by the Holter electrocardiograph. The relational expressions derived in this situation may each be expressed with a linear function or may each be expressed with a non-linear function such as a logarithmic function or exponential function.

For example, when the RR interval corresponding to one heartbeat is expressed as RR, and the QT interval is expressed as QT, the regression model with respect to state A can be expressed by using Expression (41) presented below, whereas the regression model with respect to state B can be expressed by using Expression (42) presented below.

$$QT = f1(RR) \tag{41}$$

$$QT = f2(RR) \tag{42}$$

Further, in the second embodiment, while the synchronization imaging is being performed, the second deriving function 16b is configured to judge the state of the heart of the subject and to derive data acquisition timing by using a regression model suitable for the state of the heart of the subject. More specifically, while the synchronization imaging is being performed, the second deriving function 16b judges the state of the heart of the subject and derives the data acquisition timing by selecting the regression model suitable for the judged state of the heart of the subject, from among the plurality of regression models derived by the first deriving function 16a.

For example, the second deriving function 16b judges the state of the heart of the subject, on the basis of medical examination information of the subject. In this situation, the medical examination information may be input by the operator via the input circuitry 10 or may be obtained from any of Hospital Information System (HIS) or Radiology Information Systems (RIS) via a network. After that, for example, when the state of the heart of the subject judged from the medical examination information is a normal state, the second deriving function 16b selects the regression model related to the state in which the heart is moving with a normal sinus rhythm. In contrast, when the state of the heart of the subject judged from the medical examination information is a state indicating arrhythmia, the second deriving function 16b selects the regression model related to the state in which arrhythmia is occurring.

Further, for example, every time an R-wave is detected by the ECG circuitry 18, the second deriving function 16b may derive an RR interval from the immediately-preceding R-wave to the present RR wave and judge the state of the heart of the subject on the basis of the derived RR intervals. For instance, in the example illustrated in FIG. 6, when the derived RR interval is within the range of RR interval values corresponding to state A, the second deriving function 16b determines the state of the heart of the subject to be state A. In contrast, when the derived RR interval is within the range of RR interval values corresponding to state B, the second deriving function 16b determines the state of the heart of the subject to be state B. After that, for example, the second deriving function 16b selects the regression model related to state A when the state of the heart of the subject is determined to be state A and selects the regression model related to state B when the state of the heart of the subject is determined to be state B.

In the example above, the situation is explained in which the second deriving function 16b automatically selects the regression model in accordance with the state of the heart of the subject; however, possible methods for selecting a regression model are not limited to this example. For instance, when the state of the heart of the subject has changed, the second deriving function 16b may cause the display 11 to display information indicating selectable regression models so as to receive, from the operator, an operation to select one of the displayed regression models. In that situation, the second deriving function 16b derives data acquisition timing by using the regression model selected by the operator.

Further, in the second embodiment, when the state of the heart of the subject goes into a state outside the ranges to which the regression models are applicable, the second deriving function 16b either cancels the data acquisition or discards the data acquired in the data acquisition.

For example, in the example illustrated in FIG. 6, when the RR interval derived on the basis of an R-wave detected by the ECG circuitry 18 is neither in the range of RR intervals corresponding to state A nor in the range of RR intervals corresponding to state B, the second deriving function 16b determines that the state of the heart of the subject is in a state outside the ranges to which the regression models are applicable.

Figure 7:
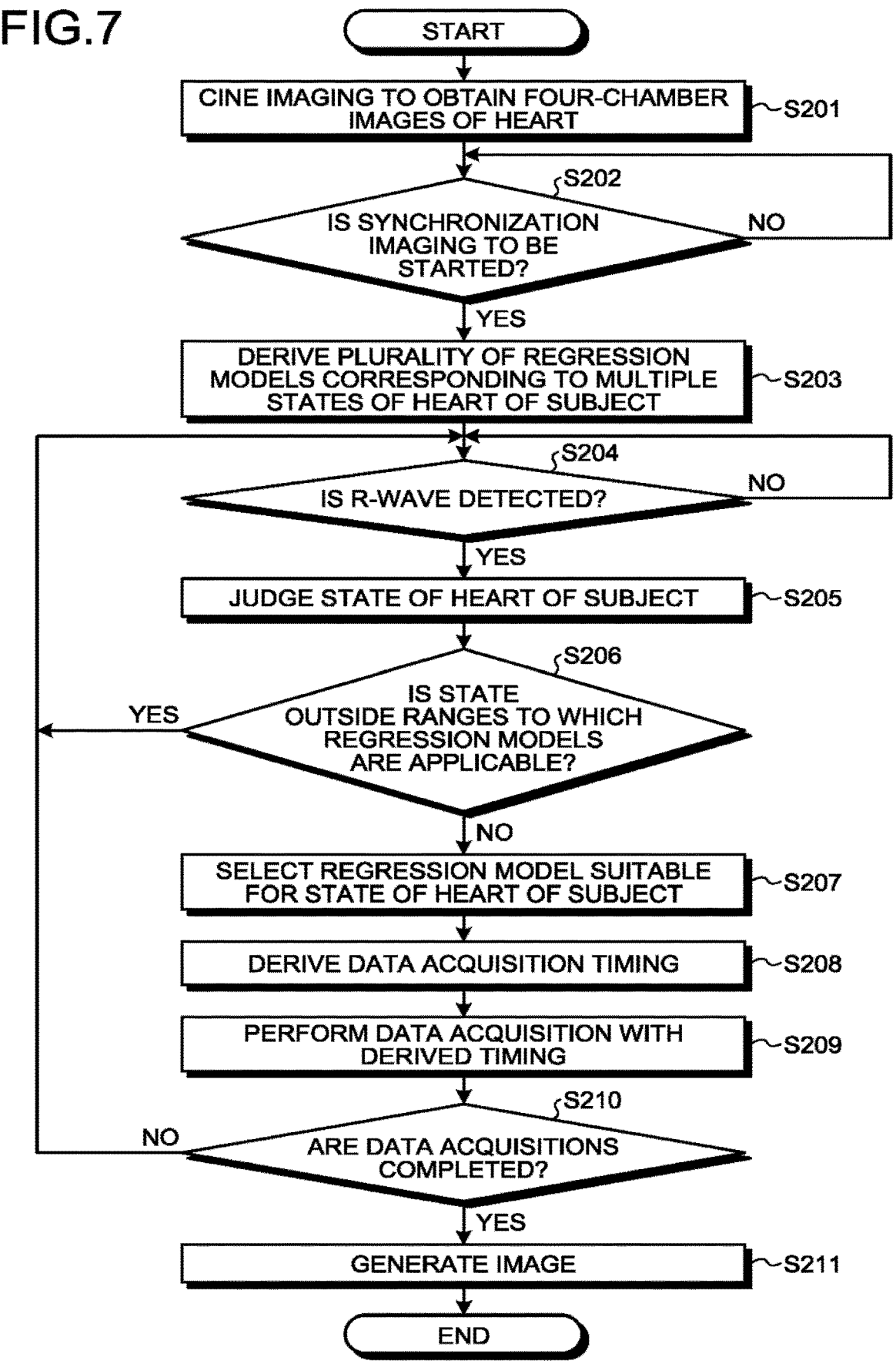
FIG. 7 is a flowchart illustrating a processing procedure in a synchronization imaging performed by an MRI apparatus according to the second embodiment.

FIG. 7 is a flowchart illustrating a processing procedure in a synchronization imaging performed by the MRI apparatus 100 according to the second embodiment. For example, as illustrated in FIG. 7, in the second embodiment, the controlling function 16c performs a cine imaging to obtain four-chamber images of the heart (step S201). The cine imaging may be performed as a part of a pre-scan performed prior to a main scan including the synchronization imaging or may be performed by itself prior to the main scan, separately from the pre-scan.

After that, when having received an instruction from the operator via the input circuitry 10 indicating that the synchronization imaging be started (step S202: Yes), the first deriving function 16a derives, as subject-specific regression models, a plurality of regression models corresponding to multiple states of the heart of the subject (step S203).

After that, when having detected an R-wave via the ECG circuitry 18 (step S204: Yes), the second deriving function 16b judges the state of the heart (step S205). In this situation, when the state of the heart of the subject is in a state outside the ranges to which the regression models are applicable (step S206: Yes), the second deriving function 16b cancels the data acquisition at this time and waits until the next R-wave is detected (return to step S204).

On the contrary, when the state of the heart of the subject is in a state within a range to which at least one of the regression models is applicable (step S206: No), the second deriving function 16b selects a regression model suitable for the state of the heart of the subject from among the plurality of regression models derived by the first deriving function 16a (step S207). After that, the second deriving function 16b derives data acquisition timing in the synchronization imaging to be performed in synchronization with heartbeats, by using the selected regression model and electrocardiographic information of the subject obtained in a real-time manner (step S208).

After that, the controlling function 16c performs a data acquisition with the timing derived by the second deriving function 16b (step S209).

In this situation, until all the data acquisitions are completed (step S210: No), the processes at steps S204 through S210 described above are repeatedly performed. After that, when all the data acquisitions are completed (step S210: Yes), the image generating function 15a generates an image of the subject on the basis of the acquired MR signal data (step S211).

According to the processing procedure described above, during the synchronization imaging, every time an R-wave is detected, the data acquisition timing is derived, during the image taking process, in a real-time manner, by using an appropriate regression model corresponding to the state of the heart of the subject, so as to perform the data acquisition.

In the processing procedure described above, the example is explained in which, when the state of the heart of the subject is in a state outside the ranges to which the regression models are applicable (see step S206), the second deriving function 16b cancels the present data acquisition; however, possible processing procedures are not limited to this example. For instance, the second deriving function 16b may instead discard the data acquired by the present data acquisition, without cancelling the data acquisition.

Further, in the processing procedure described above, the processes at steps S201 and S209 are realized, for example, as a result of the processing circuitry 16 invoking and executing a predetermined program corresponding to the controlling function 16c from the storage circuitry 12. The processes at steps S202 and S203 are realized, for example, as a result of the processing circuitry 16 invoking and executing a predetermined program corresponding to the first deriving function 16a from the storage circuitry 12. The processes at steps S204 through S208 are realized, for example, as a result of the processing circuitry 16 invoking and executing a predetermined program corresponding to the second deriving function 16b from the storage circuitry 12. The processes at steps S210 and S211 are realized, for example, as a result of the processing circuitry 15 invoking and executing a predetermined program corresponding to the image generating function 15a from the storage circuitry 12.

As explained above, the MRI apparatus 100 according to the second embodiment is configured to derive the plurality of regression models corresponding to the multiple states of the heart of the subject, as the subject-specific regression models. As a result, according to the second embodiment, even when the state of the heart of the subject changes due to a heart disease such as atrial fibrillation, arrhythmia, or the like, it is possible to perform the image taking process on the subject with appropriate timing corresponding to the change.

Third Embodiment

In the embodiments described above, the example is explained in which the data acquisition is performed during the data acquisition time period that is set in advance as an image taking condition; however, possible embodiments are not limited to this example. For instance, it is also acceptable to perform a data acquisition by deriving a data acquisition time period during an image taking process in a real-time manner for each heartbeat of the subject.

In the following sections, an example in such a situation will be explained as a third embodiment. A configuration of an MRI apparatus according to the third embodiment will be explained below, while a focus is placed on differences from the configuration of the MRI apparatus 100 illustrated in FIG. 1. Some of the constituent elements playing the same role will be referred to by using the same reference characters, and the explanations thereof will be omitted.

Figure 8:
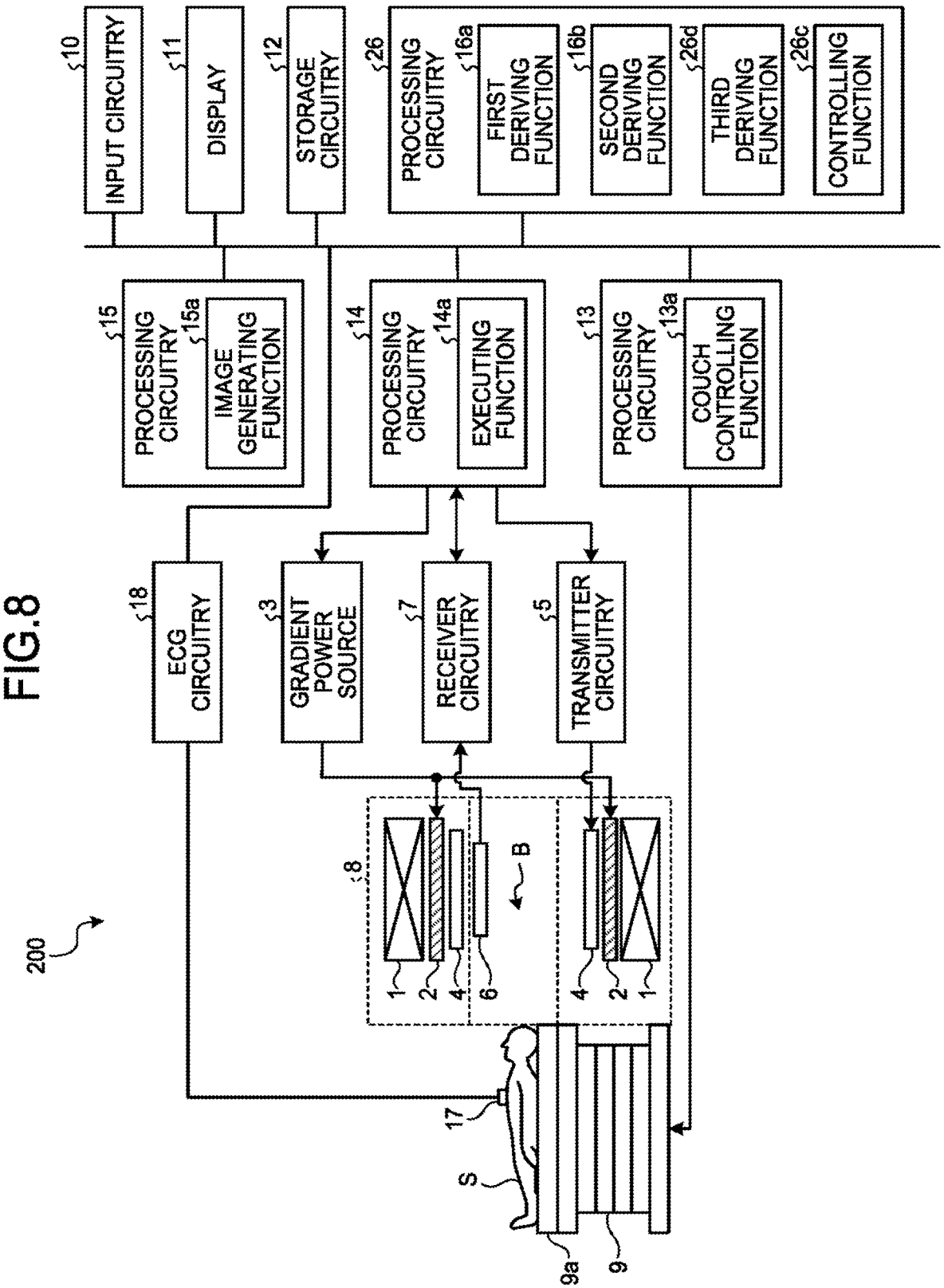
FIG. 8 is a diagram illustrating an exemplary configuration of an MRI apparatus according to a third embodiment.

FIG. 8 is a diagram illustrating an exemplary configuration of an MRI apparatus according to a third embodiment. For example, as illustrated in FIG. 8, an MRI apparatus 200 according to the third embodiment includes the static magnetic field magnet 1, the gradient coil 2, the gradient power source 3, the transmitter coil 4, the transmitter circuitry 5, the receiver coil 6, the receiver circuitry 7, the gantry 8, the couch 9, the input circuitry 10, the display 11, the storage circuitry 12, the pieces of processing circuitry 13 to 15 and another piece of processing circuitry 26, the ECG sensor 17, and the ECG circuitry 18.

In the third embodiment, the processing circuitry 26 includes a first deriving function 26a, the second deriving function 16b, a third deriving function 26d, and a controlling function 26c. The first deriving function 26a is an example of the first deriving unit. The second deriving function 16b is an example of the second deriving unit. The third deriving function 26d is an example of a third deriving unit. The controlling function 16c is an example of the controlling unit.

In the third embodiment, as a subject-specific regression model that indicates a relationship between the cardiac cycle, systole, and diastole of the subject, the first deriving function 26a further derives a mathematical function expressing a relationship between an RR interval and a TQ interval in an electrocardiographic waveform. In this situation, the TQ interval is a time interval from a T-wave to a Q-wave in one heartbeat.

For example, the first deriving function 26a derives the mathematical function expressing the relationship between the RR interval and the TQ interval, on the basis of electrocardiographic information in a predetermined time period (e.g., 24 hours) acquired from the subject by using a Holter electrocardiograph. In this situation, when the RR interval corresponding to one heartbeat is expressed as RR, while the TQ interval is expressed as TQ, the regression model derived by the first deriving function 16a can be expressed by using Expression (51) presented below.

$$TQ=g(RR) \quad (51)$$

Further, in the third embodiment, the third deriving function 26d is configured to derive a data acquisition time period in the synchronization imaging. More specifically, similarly to the second deriving function 16b, the third deriving function 26d detects the occurrence of an R-wave from a trigger signal output from the ECG circuitry 18. After that, every time the occurrence of an R-wave is detected, the third deriving function 26d derives a data acquisition time period in the synchronization imaging and notifies the controlling function 26c of the derived data acquisition time period.

For example, when the data acquisition time period with respect to an n-th heartbeat is expressed as Ta(n), the third deriving function 26d specifies, with respect to the first heartbeat (where n=1), a cardiac rest period in the cardiac cycle of the subject by using data obtained on a stage prior to the synchronization imaging and sets the specified cardiac rest period as a data acquisition time period Ta(1). In other words, with respect to the first heartbeat, the third deriving function 26d estimates the data acquisition time period in the synchronization imaging performed for the first time, by using the cardiac rest period specified from the data obtained on the stage prior to the synchronization imaging.

In this situation, for example, the third deriving function 26d determines a stationary phase by using MR images acquired by performing a cine imaging to obtain four-chamber images of the heart on the stage prior to the synchronization imaging. For example, by using the cross-sectional images corresponding to multiple temporal phases, the third deriving function 26d derives, for each of the temporal phases, a change amount in the signal intensity within the region of interest compared to the signal intensity in the immediately-preceding temporal phase and further specifics a time period in which the change amount in the signal intensity exceeds a predetermined threshold value, as the cardiac rest period.

Alternatively, the third deriving function 26d may calculate a correlation coefficient between frames by using images of the entire heart or images acquired by using only the coronary artery as a region of interest and further specify a time period corresponding to such frames of which the correlation coefficients exceed a predetermined threshold value as the cardiac rest period. Alternatively, the third deriving function 26d may specify the cardiac rest period by using a measured result obtained by an ultrasound diagnosis apparatus.

In this situation, as explained above, because the cardiac rest period can be during both diastole and systole, cardiac rest periods may be specified in both diastole and systole. In that situation, the third deriving function 26d may select one of the cardiac rest periods, depending on the heart rate of the subject. For example, when the heart rate of the subject is equal to or higher than a predetermined value, the third deriving function 26d selects the cardiac rest period during the systole, and when the heart rate of the subject is lower than the predetermined value, the third deriving function 26d selects the cardiac rest period during the diastole.

Further, for example, with respect to each of the second and later heartbeats (where n≥2), the third deriving function 26d derives the RR interval from the immediately-preceding R-wave to the present R-wave and derives a data acquisition time period by using the derived RR interval and the regression model derived by the first deriving function 16a. In other words, with respect to each of the second and later heartbeats, the third deriving function 26d estimates the data acquisition time period for the present synchronization imaging, by using the RR interval from the immediately-preceding R-wave to the present R-wave and the regression model.

For example, as indicated in Expression (52) presented below, the third deriving function 26d derives TQ(n) from the RR interval RR(n−1) from the immediately-preceding R-wave to the present R-wave, by using the regression model derived by the first deriving function 16a. In other words, the third deriving function 26d estimates TQ(n) from the actual measured value RR(n−1) by using the regression model.

$$TQ(n)=g(RR(n-1)) \quad (52)$$

After that, as indicated in Expression (53) presented below, the third deriving function 26d derives a data acquisition time period Ta(n) for the present time, from the derived value of TQ(n), the immediately-preceding data acquisition time period Ta(n−1), and the immediately-preceding TQ(n−1). In other words, the third deriving function 26d estimates Ta(n) by using the actual measured values Ta(n−1) and TQ(n−1), as well as TQ(n) estimated from another actual measured value.

$$Ta(n)=Ta(n-1)\times TQ(n)/TQ(n-1) \quad (53)$$

As explained above, with respect to each of the second and later heartbeats, the data acquisition time period is derived during the image taking process in a real-time manner, in accordance with the actual measured RR interval and the immediately-preceding data acquisition time period.

Further, in the third embodiment, the controlling function 26c controls the synchronization imaging so that the data acquisitions are performed with the timing derived by the second deriving function 16b and also controls the synchronization imaging so that the data acquisitions are performed for the data acquisition time periods derived by the third deriving function 26d.

More specifically, in the same manner as in the embodiments described above, every time an elapsed time period indicating data acquisition timing is provided as a notification from the second deriving function 16b, the controlling function 26c transmits, to the processing circuitry 14, sequence execution data generated on the basis of the image taking condition, at the point in time when the elapsed time period has elapsed since the time at which the notification was provided. In this situation, in the third embodiment, the controlling function 26c generates the sequence execution data so that the data acquisition is performed for the data acquisition time period derived by the third deriving function 26d. As a result, the data acquisition to acquire MR signal data is performed for the data acquisition time period derived by the third deriving function 26d, starting at the point in time when the elapsed time period derived by the second deriving function 16b has elapsed since the point in time at which the R-wave was detected.

As explained above, the MRI apparatus 100 according to the third embodiment is configured to derive the data acquisition time periods in the synchronization imaging. Consequently, according to the third embodiment, even when the state of the heart of the subject changes during the execution of the synchronization imaging, it is possible to perform each of the data acquisitions for an appropriate data acquisition time period in accordance with the change.

Other Embodiments

It is also possible to carry out any of the embodiments of the MRI apparatus described above by modifying a part of the configurations thereof as appropriate, depending on usage and purposes. In the following sections, a number of modification examples related to the MRI apparatus described above will be explained as other embodiments.

For example, in the embodiments described above, the example is explained in which the second deriving function 16b estimates the data acquisition timing by using the regression model derived on the basis of the electrocardiographic information acquired from the subject by the Holter electrocardiograph; however, because cardiac physiological hysteresis (QT/RR hysteresis) is present in the relationship between RR intervals and QT intervals in electrocardiographic waveforms, there is a possibility that an error may occur in the QT intervals estimated from the regression model in some situations.

Figure 9:
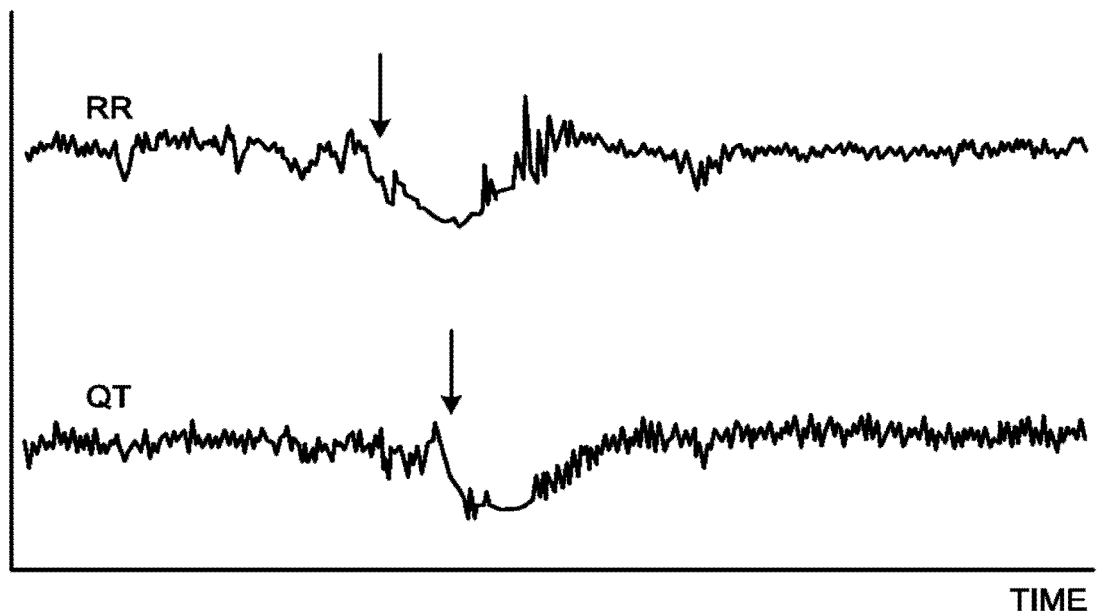
FIG. 9 is a drawing illustrating an example of hysteresis related to an MRI apparatus according to another embodiment.

FIG. 9 is a drawing illustrating an example of hysteresis related to an MRI apparatus according to another embodiment. In this situation FIG. 9 illustrates measured results of RR intervals and QT intervals in a plurality of consecutive heartbeats that are measured in a predetermined time period.

For example, as illustrated in FIG. 9, it is known that RR intervals and QT intervals do not fluctuate in temporally the same manner as each other and that QT intervals fluctuate later than RR intervals do, an exponential change is observed therein, and the change is vary among subjects. For example, as indicated with an arrow in FIG. 9, it is known that the timing with which QT intervals start changing drastically is later than the timing with which RR intervals start changing drastically.

For this reason, for example, when a regression model being used is derived on the basis of electrocardiographic information acquired from the subject during a time period in which RR intervals and QT intervals are relatively stable, there is a possibility that, in some situations, an error may occur between the QT intervals estimated from the regression model and the actual QT intervals.

To cope with this situation, for example, the first deriving function 16a may be configured to derive the regression model in considering of subject-specific QT/RR hysteresis.

For example, the first deriving function 16a derives a mathematical function expressing a relationship between an RR interval and a QT interval in considering of subject-specific QT/RR hysteresis.

In that situation, for example, the first deriving function 16a derives, on the basis of the electrocardiographic information acquired from the subject, for each heartbeat i, $\overline{RR}_i$ that is a linearly or exponentially weighted average of RR intervals, by using Expression (61) presented below.

$$\overline{RR}_i = \sum_{j=-N+1}^{0} w_j RR_{i+j} \quad (61)$$

Herein, $RR_{i+j}$ expresses an RR interval at a heartbeat i+j. N expresses an average of all $N_i$, when $N_i$ expresses a number of heartbeats occurred within a given window length set as preceding a heartbeat i. j expresses a time interval between two heartbeats represented, which is expressed by a number of heartbeats, and $W_j$ expresses a weighting coefficient which represents a weight for deriving the weighted average with respect to the time interval j.

Figure 10:
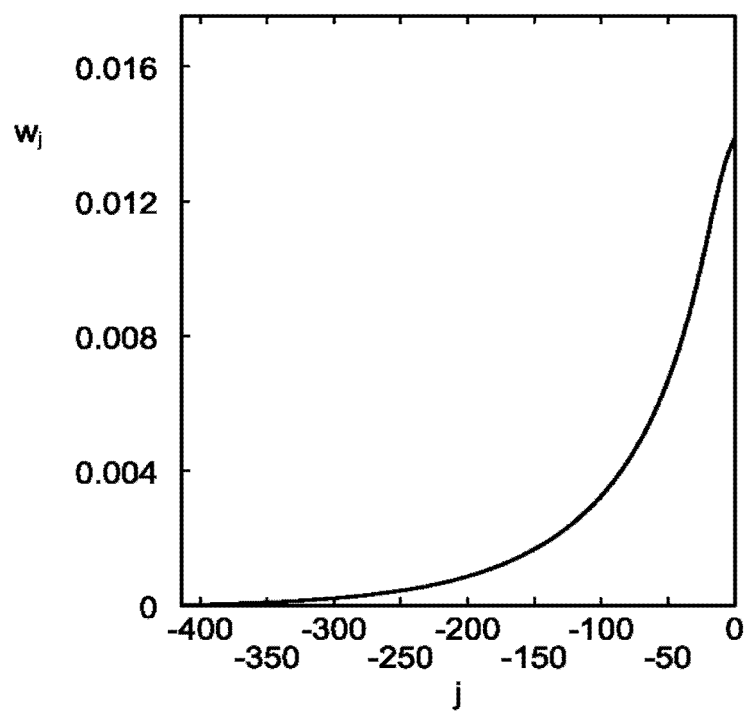
FIG. 10 is a drawing illustrating an example of weighting coefficients used in a process of deriving weighted averages of RR intervals performed by the MRI apparatus according to the other embodiment.

FIG. 10 is a drawing illustrating an example of weighting coefficients used in a process of deriving weighted averages of RR intervals performed by the MRI apparatus according to the other embodiment.

For example, as illustrated in FIG. 10, weighting coefficients $w_j$ are set so that they exponentially decrease as time interval j increases. Thereby, when lapse time from a change of RR interval becomes shorter, the value of weighting coefficients $w_j$ becomes relatively large, and when lapse time from a change of RR interval becomes longer, the value of weighting coefficients $w_j$ becomes relatively small.

Then, the first deriving function 16a fits a mathematical function expressed by using Expression (62) presented below to the distribution of the values of the derived $\overline{RR}_i$ and the QT intervals, and thereby derives the regression model in considering of subject-specific QT/RR hysteresis.

$$QT_i = \beta(\overline{RR}_{Xi})^\alpha \quad (62)$$

Specifically, the first deriving function 16a derives the regression model by calculating the coefficients α and β by implementing a least squares method while substituting the derived $\overline{RR}_i$ and the QT intervals to $\overline{RR}_{Xi}$ and $QT_i$, respectively.

In the regression model derived in this way, since the weighting coefficients $w_j$ are set so that they exponentially decrease as time interval j increases as illustrated in FIG. 10, the value of the QT interval varies in accordance with the lapse time from a change of RR interval. Accordingly, the regression model derived in this embodiment becomes a regression model taking account of the QT/RR hysteresis. Thereby, it is possible to estimate the QT interval more appropriately.

According to the configuration described above, it is possible to correct the relationship between the RR intervals and the QT intervals caused by the cardiac physiological hysteresis, and thereby it is possible to improve data collection efficiency and to perform the data acquisitions with more appropriate timing. Further, according to the above configuration described above, QT intervals corresponding to mutually the same RR interval have values close to each other (see FIG. 12).

Further, to cope with this situation, for example, the second deriving function 16b may be configured to derive the interval between the boundary of systole and diastole and a predetermined waveform by using the regression model and, when the difference between the derived value and the actual value of the interval is outside a tolerated range, to either cancel the data acquisition or discard the data acquired in the data acquisition. In this situation, the interval between the boundary between systole and diastole and the predetermined waveform may be, for example, a QT interval, a TR interval, a TP interval, or a TQ interval explained above.

For example, when using a mathematical function expressing the relationship between an RR interval and a QT interval as the regression model, the second deriving function 16b measures, after the synchronization imaging is started, the QT interval for each of the heartbeats, on the basis of the electrocardiographic signal detected by the ECG sensor 17 and the ECG circuitry 18. After that, for each of the heartbeats, the second deriving function 16b compares the QT interval derived by using the regression model with respect to the heartbeat with the actual measured QT interval, and when the difference between the two is outside the tolerated range, the second deriving function 16b either cancels the data acquisition or discards the data acquired in the data acquisition.

In that situation, the tolerated range related to the difference of the QT intervals may be, for example, a range set with an upper limit value calculated by adding 10% to the QT interval value derived by using the regression model and a lower limit value calculated by subtracting 10% from the QT interval value.

By using this configuration, it is possible to correct the relationship between the RR intervals and the QT intervals caused by the cardiac physiological hysteresis, by adopting only such QT intervals that are within the tolerated range, among the QT interval derived by using the regression model.

Figure 11:
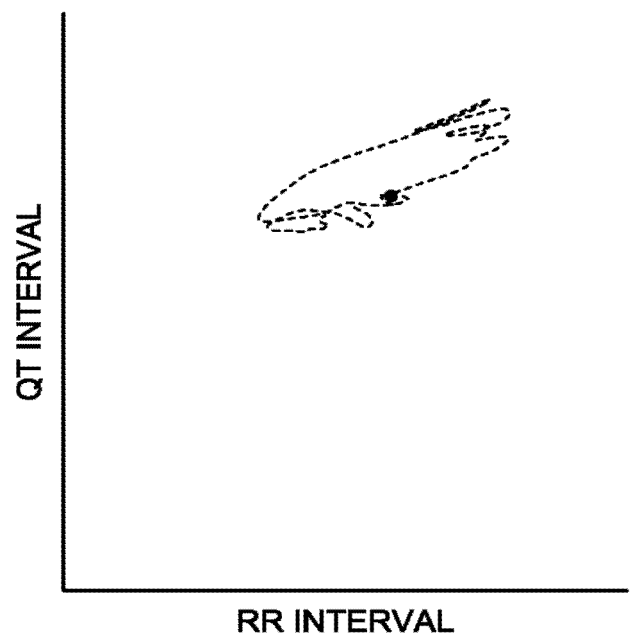
FIG. 11 is a drawing illustrating an example of a process of correcting a relationship between RR intervals and QT intervals performed by the MRI apparatus according to the other embodiment.
Figure 12:
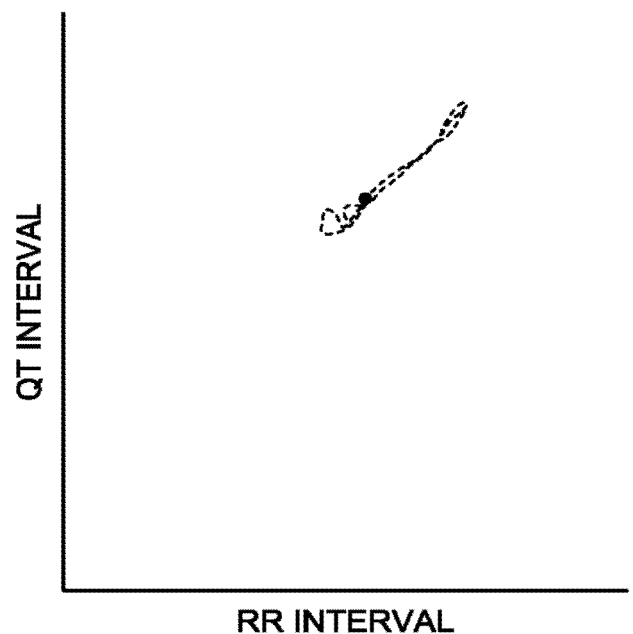
FIG. 12 is another drawing illustrating the example of the process of correcting the relationship between the RR intervals and the QT intervals performed by the MRI apparatus according to the other embodiment.

FIGS. 11 and 12 are drawings illustrating an example of the process of correcting the relationship between the RR intervals and the QT intervals performed by the MRI apparatus according to the other embodiment. In this situation, FIG. 11 illustrates a distribution of RR intervals and QT intervals that would be used when no judgment is made as to whether the QT intervals derived by using the regression model are appropriate or not. In contrast, FIG. 12 illustrates a distribution of RR intervals and QT intervals that are used when, as in the present embodiment, the judgment is made as to whether the QT intervals derived by using the regression model are appropriate or not.

For example, as illustrated in FIG. 12, when the above-mentioned configuration is used, QT intervals corresponding to mutually the same RR interval have values close to each other, because only such QT intervals that are in the tolerated range are adopted. With this arrangement, it is possible to absorb the errors that may be caused in the relationship between the RR intervals and the QT intervals by the cardiac physiological hysteresis. It is therefore possible to perform the data acquisition with more appropriate timing.

Further, in the embodiments described above, the example is explained in which the first deriving function 16a derives the regression model expressed with a linear function, a logarithmic function, an exponential function, or the like; however, it is expected that the relationship among the cardiac cycle, systole, and diastole of individual subjects exhibit various patterns for different subjects.

To cope with this situation, for example, the first deriving function 16a may be configured to select a template that best matches the electrocardiographic information acquired from the subject, from among a plurality of types of templates on which the regression model is based and to further derive a subject-specific regression model on the basis of the selected template.

For example, when deriving a mathematical function expressing the relationship between an RR interval and a QT interval as the regression model, the first deriving function 16a derives a subject-specific regression model, by selecting a template that approximates, with the highest level of precision, the distribution of values of the RR intervals and the QT intervals corresponding to the heartbeats included in the electrocardiographic information of a predetermined time period acquired from the subject by using a Holter electrocardiograph, from among a plurality of types of templates expressed with a plurality of mutually-different expressions (71) to (80) as presented below.

Linear:
$$QT=\beta+\alpha RR \tag{71}$$

Hyperbolic:
$$QT=\beta=(\alpha/RR) \tag{72}$$

Parabolic Log/Log:
$$QT=\beta(RR)^\alpha \tag{73}$$

Logarithmic:
$$QT=\beta+\alpha \ln(RR) \tag{74}$$

Shifted Logarithmic:
$$QT=\ln(\beta+\alpha RR) \tag{75}$$

Exponential:
$$QT=\beta+\alpha e^{-RR} \tag{76}$$

Arcus Tangent:
$$QT=\beta+\alpha \ arctag(RR) \tag{77}$$

Hyperbolic Tangent:
$$QT=\beta+\alpha tgh(RR) \tag{78}$$

Arcus Hyperbolic Sine:
$$QT=\beta+\alpha \ arcsin \ h(RR) \tag{79}$$

Arcus Hyperbolic Cosine:
$$QT=\beta+\alpha \ arccos \ h(RR+1) \tag{80}$$

For example, the first deriving function 16a has the templates fitted to the distribution of the values of the RR intervals and the QT intervals, by calculating the coefficients $\alpha$ and $\beta$ included in the expressions of the templates, by implementing a least squares method. After that, the first deriving function 16a derives the subject-specific regression model by selecting a template having the highest degree of correlation (having a correlation coefficient r closest to 1, for example) with the distribution of the values of the RR intervals and the QT intervals, from among the templates that have been fitted.

By using this configuration, it is possible to derive a more appropriate regression model for each subject, by performing the analysis and the comparison in a comprehensive manner while using the plurality of types of templates.

Further, in the embodiments above, the example is explained in which the first deriving function 16a derives the regression model on the basis of the electrocardiographic information in the predetermined time period acquired from the subject by using the Holter electrocardiograph. However, depending on the situation, there is a possibility that the section from which the electrocardiographic information was obtained may not be sufficient. For example, when a mathematical function expressing the relationship between an RR interval and a QT interval is derived as the regression model, there is a possibility that the values of the RR intervals or the QT intervals may have not been obtained from a sufficiently large section.

In that situation, in the regression model derived by the regression analysis, the section in which no electrocardiographic information was obtained would be complemented with information through an extrapolation process and would have a lower reliability than the sections in which certain values are obtained.

To cope with this situation, for example, the second deriving function 16b may be configured to derive the interval between the boundary between systole and diastole and a predetermined waveform by using the regression model and, when the derived value is outside a tolerated range, to either cancel the data acquisition or discard the data acquired in the data acquisition. In this situation, the interval between the boundary between systole and diastole and the predetermined waveform may be, for example, a QT interval, a TR interval, a TP interval, or a TQ interval explained above.

For example, when using a mathematical function expressing the relationship between an RR interval and a QT interval as the regression model, the second deriving function 16b measures, after the synchronization imaging is started, the QT interval for each of the heartbeats, on the basis of the electrocardiographic signal detected by the ECG sensor 17 and the ECG circuitry 18. After that, for each of the heartbeats, the second deriving function 16b judges whether or not the QT interval derived by using the regression model with respect to the heartbeat is within the tolerated range, and when the QT interval is outside the tolerated range, the second deriving function 16b either cancels the data acquisition or discards the data acquired in the data acquisition.

In this situation, the tolerated range with respect to the QT interval may be, for example, a range defined with an upper limit value and a lower limit value of QT intervals obtained from a general standpoint based on cardiac physiology.

With the configuration described above, among the QT intervals derived by using the regression model, only such QT intervals that have a high reliability are adopted. Accordingly, even when the electrocardiographic information of the subject has not been obtained from a sufficiently large section, it is possible to perform the data acquisition with more appropriate timing.

It is possible to carry out any of the embodiments described above individually or in combination, as appropriate.

In the embodiments described above, the example is explained in which the R-wave is detected by using the ECG sensor; however, possible embodiments are not limited to this example. For instance, it is also acceptable to detect the R-wave by combining an ECG sensor with a photoplethysmogram (PPG) sensor.

In the embodiments above, the examples in which the present disclosure is applied to an MRI apparatus are explained. However, possible embodiments are not limited to those examples. For instance, the synchronization imaging described above is similarly applicable to other medical image diagnosis apparatuses such as X-ray Computed Tomography (CT) apparatuses, Positron Emission Tomography (PET) apparatuses, X-ray diagnosis apparatuses, ultrasound diagnosis apparatuses, and the like.

The term "processor" used in the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage circuitry 12, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

According to at least one aspect of the embodiments described above, it is possible to provide a magnetic resonance imaging apparatus capable of performing the image taking process on the subject with the appropriate timing corresponding to the fluctuation of subject-specific heartbeats.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising processing circuitry configured:
    to derive a plurality of regression models in accordance with a plurality of states of a heart of a subject indicated by electrocardiographic information acquired from the subject, by performing a regression analysis based on a distribution of values of periods of systole and diastole for each heartbeat of a plurality of heartbeats included in the electrocardiographic information, each of the plurality of regression models being expressed by a relational expression that is specific to a subject and that indicates a relationship between a period of a cardiac cycle and periods of systole and diastole in the cardiac cycle of a heart of the subject; and
    to, after the plurality of regression models are derived and while a synchronization imaging that is performed in synchronization with heartbeats of the heart of the subject is being performed, with respect to each of the heartbeats, judge a state of the heart of the subject, select at least one regression model suitable for the judged state of the heart of the subject from the derived plurality of regression models, derive a start time of a data acquisition in the synchronization imaging, by using the selected at least one regression model and electrocardiographic information of the subject obtained during the synchronization imaging, and control the synchronization imaging so that the data acquisition is performed with the derived start time.

2. The medical image diagnosis apparatus according to claim 1, wherein, after the plurality of regression models are derived and while the synchronization imaging is being performed, with respect to each of the heartbeats, the processing circuitry further derives a data acquisition time period in the synchronization imaging, and controls the synchronization imaging so that the data acquisition is performed for the derived data acquisition time period.

3. The medical image diagnosis apparatus according to claim 1, wherein the relationship is related to a boundary between the periods of the systole and the diastole.

4. The medical image diagnosis apparatus according to claim 3, wherein the boundary is a T-wave in an electrocardiographic waveform.

5. The medical image diagnosis apparatus according to claim 1, wherein, while the synchronization imaging is being performed, the processing circuitry corrects the selected regression model in accordance with a result of judging the state of the heart of the subject.

6. The medical image diagnosis apparatus according to claim 1, wherein when the state of the heart of the subject goes into a state outside a range to which the selected regression model is applicable, the processing circuitry either cancels the data acquisition or discards data acquired by the data acquisition.

7. The medical image diagnosis apparatus according to claim 1, wherein the processing circuitry determines a stationary phase of the heart of the subject by using data obtained prior to the synchronization imaging, and then derives the start time of the data acquisition by using the determined stationary phase and the selected regression model.

8. The medical image diagnosis apparatus according to claim 1, wherein, while the synchronization imaging is being performed, the processing circuitry determines a stationary phase of the heart of the subject, and then derives the start time of the data acquisition by using the determined stationary phase and the selected regression model.

9. The medical image diagnosis apparatus according to claim 1, wherein, as each of the plurality of regression models, the processing circuitry derives a mathematical function expressing a relationship between an RR interval and a QT interval in an electrocardiographic waveform.

10. The medical image diagnosis apparatus according to claim 1, wherein, as each of the plurality of regression models, the processing circuitry derives a mathematical function expressing a TP interval in an electrocardiographic waveform, from a relationship between an RR interval and a PT interval in an electrocardiographic waveform.

11. The medical image diagnosis apparatus according to claim 1, wherein the processing circuitry derives the plurality of regression models on a basis of the electrocardiographic information in a predetermined time period acquired from the subject by using a Holter electrocardiograph.

12. The medical image diagnosis apparatus according to claim 1, wherein, as each of the plurality of regression model, the processing circuitry derives a mathematical function expressing a relationship between an RR interval and a QT interval in considering of subject-specific QT/RR hysteresis.

13. The medical image diagnosis apparatus according to claim 12, wherein the processing circuitry derives an interval between a boundary between the systole and the diastole and a predetermined waveform by using the selected regression model and, when a difference between a derived value of the interval and an actual measured value of the interval is outside a tolerated range, the processing circuitry either cancels the data acquisition or discards data acquired in the data acquisition.

14. The medical image diagnosis apparatus according to claim 1, wherein the processing circuitry selects a template that best matches the electrocardiographic information acquired from the subject, from among a plurality of types of templates on which the selected regression model is based, and then derives the plurality of regression models as subject-specific regression models on a basis of the selected template.

15. The medical image diagnosis apparatus according to claim 1, wherein the processing circuitry derives an interval between a boundary between the systole and the diastole and a predetermined waveform by using the selected regression model and, when a derived value of the interval is outside a tolerated range, the processing circuitry either cancels the data acquisition or discards data acquired in the data acquisition.

16. The medical image diagnosis apparatus according to claim 1, wherein a first state of the plurality of states is normal sinus rhythm.

17. The medical image diagnosis apparatus according to claim 16, wherein a second state of the plurality of states is a state indicating arrhythmia is occurring.

18. The medical image diagnosis apparatus according to claim 16, wherein a second state of the plurality of states is a state indicating bradycardia arrhythmia is occurring.

19. The medical image diagnosis apparatus according to claim 1, wherein the processing circuitry is further configured:
to, prior to the synchronization imaging, perform cine imaging to obtain slice images of the heart;
to, after the synchronization imaging is started, derive the plurality of regression models; and
to, while the synchronization imaging is being performed, detect a predetermined wave in an electrocardiographic waveform of the heart;
to, with respect to each time the predetermined wave is detected, judge a state of the heart, select the at least one regression model, derive the start time of the data acquisition by using the selected at least one regression model, the electrocardiographic information of the subject obtained during the synchronization imaging and a stationary phase of the heart determined based on the slice images, and control the synchronization imaging.

* * * * *